United States Patent
Newkome et al.

(10) Patent No.: US 6,566,409 B1
(45) Date of Patent: *May 20, 2003

(54) LOCK AND KEY MICELLES

(75) Inventors: George R. Newkome, Temple Terrace, FL (US); Charles N. Moorefield, Tampa, FL (US); Gregory Baker, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/567,447

(22) Filed: May 8, 2000

Related U.S. Application Data

(60) Division of application No. 09/066,192, filed on Apr. 24, 1998, now Pat. No. 6,130,209, which is a division of application No. 08/704,813, filed on Aug. 28, 1996, now Pat. No. 5,863,919, which is a continuation-in-part of application No. 08/280,591, filed on Jul. 25, 1994, now Pat. No. 5,650,101.

(51) Int. Cl.$^7$ .......................... B01F 17/30; B01J 13/00; C07C 239/02; C02F 5/12
(52) U.S. Cl. ...................... 516/70; 252/180; 424/1.53; 424/DIG. 16; 525/936; 530/816; 546/308; 564/160
(58) Field of Search ............................ 252/180, 182.23, 252/182.28; 264/4.3; 428/402.21, 402.22; 525/903, 936; 424/1.53, 497, DIG. 16; 436/829; 530/816; 546/308; 564/142, 160; 514/51, 256, 259, 269, 270, 483; 516/70; 536/26.1

(56) References Cited

U.S. PATENT DOCUMENTS

| | | | |
|---|---|---|---|
| 2,461,119 A | 2/1949 | Lott et al. ................... 546/308 |
| 3,910,847 A | 10/1975 | Thompson ................... 252/77 |
| 4,288,592 A | 9/1981 | Rauhut et al. ........... 564/142 X |
| 4,435,548 A | 3/1984 | Tomalia ....................... 525/451 |
| 4,468,499 A | 8/1984 | Siegfried et al. ........... 525/301 |
| 4,469,621 A | 9/1984 | Kunitake et al. ........... 516/199 |
| 4,507,466 A | 3/1985 | Tomalia ....................... 528/332 |
| 4,558,120 A | 12/1985 | Tomalia ....................... 528/363 |
| 4,568,737 A | 2/1986 | Tomalia ....................... 528/332 |
| 4,587,329 A | 5/1986 | Tomalia ....................... 528/363 |
| 4,631,337 A | 12/1986 | Tomalia ....................... 528/391 |
| 4,694,064 A | 9/1987 | Tomalia ....................... 528/332 |
| 4,713,975 A | 12/1987 | Tomalia et al. ............ 73/865.8 |
| 4,737,550 A | 4/1988 | Tomalia ....................... 525/418 |
| 5,154,853 A | 10/1992 | Newkome .................... 252/311 |
| 5,221,534 A | 6/1993 | DesLauriers et al. ..... 424/78.03 |
| 5,422,379 A | 6/1995 | Newkome et al. ............ 521/53 |
| 5,585,457 A | * 12/1996 | Newkome et al. .......... 528/353 |
| 5,650,101 A | 7/1997 | Newkome et al. ........... 264/4.3 |
| 5,863,919 A | * 1/1999 | Newkome et al. .......... 514/256 |
| 6,130,209 A | * 10/2000 | Newkome et al. ............ 514/51 |
| 6,248,306 B1 | * 6/2001 | Schmitt-Willich et al. ....... 424/DIG. 16 |

OTHER PUBLICATIONS

1(a) Mittal et al., "The Wide World of Micelles", Micellization, Solubilization, and Microemulsions, NY, vol. 1, pp. 1–21 (1977).
1(b) Tanford, C. "Micelles" The Hydrophobic Effect: Formation of Micelles and Biological Membranes, 2nd Ed., Wiley–Interscience New York, pp 42–59 (1980).
1(c) Ringsdorf et al., "Molecular Architecture/Function of Polymeric Oriented Systems: Models for Study of Org., Surface Recognition and Dynamics of Biomembranes", Angew Chem. Ed. Engl. 27:113–158 (1988).
2. Menger, F. "Groups of Organic Molecules That Operate Collectively" Angew. Chem. Int. Ed. Engl., 30:1086–1099 (1991).
3(a) Mekelburger et al., "Dendrimers, Arborols, Cascade Molecules: Breakthrough into Generations of New Materials", Angew. Chem. Int. Ed. Engl., 31:1571–1576 (1992).
3(b) Buhleier et al., "Cascade– and "Nonskid–Chain–Like" Syntheses of Molecular Cavity Topologies" Synthesis, 155–158 (1978).
4. Newkome et al. "Building Blocks for Dendritic Macromolecules" Aldrichimica Acta, 25:31–38 (1992).
5. Newkome et al., "Alkane Cascade Polymers Possession Micellar Topology: Micellanoic Acid Derivatives" Angew. Chem. Int. Ed. Eng. 30:1176–1180 (1991).
6. Newkome et al., "Unimolecular Micelles" Angew. Chem. Int. Ed. Engl. 30:1178–1180 (1991).
7(a) Tomalia, "Conformational Calculations on Plly–di–n–hexylsilane" Macromolecules, 20:1167–1169 (1987).
7(b) Tomalia et al., "Dendritic Macromolecules: Synthesis of Starburst Dendrimers" Macromolecules, 19:2466–2468 (1986).
7(c) Tomalia et al., "Starburst Dendrimers. 3. The Importance of Branch Junction Symmetry in the Dev. of Topological Shell Molecules" J.Am.Chem.Soc., 198:1601–1603 (1987).

(List continued on next page.)

Primary Examiner—Richard D. Lovering
(74) Attorney, Agent, or Firm—Kohn & Associates, PLLC

(57) ABSTRACT

A lock unimolecular micelle includes at least one engineered acceptor specifically binding a ligand (or specifically a "key" unimolecular micelle) thereto. A key unimolecular micelle comprises a core molecule and a plurality of branches extending therefrom, at least one of the branches including a shank portion extending therefrom having a terminal moiety at an end thereof for binding to a complimentary acceptor of a lock unimolecular micelle. Together, the lock and key micelles form a unit, either irreversibly or reversibly bound wherein the lock micelles is a soluble receptor engineered to specifically bind to the specifically engineered key micelle.

16 Claims, 12 Drawing Sheets

OTHER PUBLICATIONS

8. Pessi et al., "Appl. of Cont–flow Polyamde Method to Solid–phase Synth. of Multiple ANtigen Peptide (MAP) based on Deq. of Malaria Epitope" J.Chem.Soc.Chem.Commun. pp. 8–9 (1990).
9. Padias et al., "Starburst Polyether Dendrimers", J.Org.Chem., 55:5305–5312 (1987).
10. Bochkov et al., "Synthesis of Cascadol, A Highly Branched Functionalized Polyether" translated from Izvestiya Akademii Nauk SSSR, Seriya Khimicheskaya, No. 10, pp. 2394–2395 (1989).
11. Rengan and Engel, "Phosphonium Cascade Molecules", J.Chem.Soc.Chem.Commun. pp. 1084–1085 (1990).
12. Uchida, "General Strategy for Systematic Synthesis of Oligosiloxanes, Silicone Dendrimers", J.Am.Chem.Soc., 112:7077–7079 (1990).
13. Bochkarev et al., "Polyphenylenegermane—a new type of polymeric" Journal on Organometallic Chemistry, 195–200 (1987) [not translated; only copy available].
14(a) Wooley, "Polymers with Cont. Molecular Architecture: Cont. of Surface Functionality in Synthesis of Dendritic Hyperbranched Macromolecule" J.Chem.Soc.Perkin Trans.1, pp. 1059–1075 (1991).
14(b) Hawker and Frechet, "Preparation of Polymers with Contr. Molecular Architecture: A New Convergent Approach to Dendritic Macromolecules" J.Am.Chem.Soc., 112:7638–7647 (1990).
14(c) Hawker and Frechet, "Control of Surface Functionality in Synthesis of Dendritic Macromolecules . . . " Macromolecules 23:4726–4729 (1990).
15(a) Rajca, "Synthesis of 1,3–Connected Polyarylmethanes", J.Org.Chem. 56:2557–2563 (1991).
15(b) Rajac, "A Polyarylmethyl Carbotetraanion", J.Am.Chem.Soc. 5889–5890 (1990).
16. Kim et al. "Water–Soluble Hyperbranched Polyphenylene: A Unimolecular Micelle", J.Am.Chem.Soc. 112, 4592–4593 (1990).
17. Miller et al., "Convergent Synthesis of Monodisperse Dendrimers Based Upon 1,3,5–Trisubstituted Benzenes" Chem.Mater., vol. 2, No. 4, 347–349 (1990).
18(a) Shahlai et al., "Supertriptycene . . . " J.Am.Chem.Soc., 112:3678–3688 (1990).
18(b) Singh et al., "Extensions of Micycloalkyne . . . " J.Org.Chem. 55:3412 (1990).
19. Moore and Xu, "Synthesis of Rigid Dentritic Macromolecules: Enlarging Repeat Unit Size as Function of Generation Permits Growth to Continue" Macromolecules, 24:5893–5894 (1991).
20. Lakowicz, J.R. et al., Biochem. 1985, 24, 376–383.
21. Shinaki, S. et al., J. Am. Chem. Soc. 1986, 108, 2409; Brooker et al., J. Am. Chem. Soc. 1941, 63, 3214.
22/24 Menger et al., J. Am. Chem. Soc., 1981, 103, 5938–5939.
23. Saunders et al. Planta 1981, 152, 272–281.
Mathias et al., "Self–Assembly Through Hydrogen Bonding: Peripheral Crowding—A New Strategy . . . " J.Am.Chem.Soc., 1994, 116, 4326–4340.
Murray et al., "New Triply Hydrogen Bonded Complexes with Highly Variable Stabilities" J.Am.Chem.Soc. 1992, 114, 4010–4011.
Young et al., "Smart" Cascade Polymers, Modular Syntheses of Four–Directional Dendritic . . . Macromolecules 1994, 27, 3464–3471.

\* cited by examiner

LOCK AND KEY MICELLES

CROSS-REFERENCE TO RELATED APPLICATIONS

This application is a division of U.S. Ser. No. 09/066,192, filed Apr. 24, 1998, now U.S. Pat. No. 6,130,209, issued Oct. 10, 2000, which is a division of U.S. Ser. No. 08/704,813, filed Aug. 28, 1996, now U.S. Pat. No. 5,863,919, issued Jan. 26 1997, which is a continuation-in-part of U.S. Ser. No. 08/280,591, filed Jul. 25, 1994, now U.S. Pat. No. 5,650,101, issued Jul. 22, 1997, all of which are incorporated herein by reference.

GRANT REFERENCE

The research carried out in connection with this invention was supported in part by a grant from the National Science Foundation (DMR-92-17331; 92-08925) and The U.S. Army Office of Research (DAAHO$-93-0048). The Government has certain rights in the invention.

TECHNICAL FIELD

The present invention relates to highly-branched molecules possessing a predetermined three-dimensional morphology, referred to as unimolecular micelles. More specifically, the present invention relates to micelles having uses in areas such as radio-imaging, drug delivery, catalysis, affinity filtration for separating enantiomers and the like and other areas.

BACKGROUND OF THE INVENTION

Neat and orderly arrays for micellar systems have been reported,[1,2] and are structurally based on the original work of Vögtle et al.,[3a] who delineated "cascade" construction.

The U.S. Pat. No. 4,435,348, issued Mar. 6, 1984; U.S. Pat. No. 4,507,466, issued Mar. 26, 1985; U.S. Pat. No. 4,558,120, issued Dec. 10, 1985; U.S. Pat. No. 4,568,737, issued Feb. 4, 1986; U.S. Pat. No. 4,587,329; issued May 6, 1986; U.S. Pat. No. 4,631,337, issued Dec. 23, 1986; U.S. Pat. No. 4,694,064, issued Sep. 15, 1987; and U.S. Pat. No. 4,737,550, issued Apr. 12, 1988, all to Tomalia et al., relate to branched polyamidoamines. The polyamidoamines include a plurality of pendent aminoamide moieties exhibiting properties which are related to linear polyamidoamines from which the branched polymers are derived. These compounds can be characterized as high molecular weight, highly-branched, multi-functional molecules possessing a three-dimensional morphology. Synthetic strategies employed for the realization of such "cascade polymers"[3b] require consideration of diverse factors including the content of the initial core, building blocks, space for molecules, branching numbers, dense packing limits, and desired porosity, as well as other factors.[4] The selection of the building blocks govern the type of branching desired from the core molecule, as well as the technology used to attach each successive layer or "tier" of the cascade polymer.

Applicants have developed a novel method of making cascade polymers, especially those providing a unimolecular micelle consisting essentially of alkyl carbon possessing diverse terminal functionality. Such compounds are disclosed in U.S. Pat. No. 5,154,853 (1992) to applicants.

Further developments of the above-described chemistry by applicants have demonstrated that the unimolecular micellar character permits the initial evaluation of the orderliness and chemistry within a series of specifically designed, spherical macromolecules due to covalently bound assemblies of internal reactive sites.[5,6] Similar dendritic species have been constructed with amide,[4,7,8] ethereal,[9,10] phosphonium,[11] silicone,[12] germane,[13] and aryl,[14-19] inner linkages and functionalities.

Out of all these systems, however, it has been determined that only three systems thus far created have the potential to undergo specifically located chemical modification within the inner lipophilic regions thereof. When there is actual space within these regions, these lipophilic regions are termed "void regions". The sum of the "void regions" constitutes the total "void volume" of the cascade polymer. The presently known compounds having such inner void regions capable of covalent modification are the hydrocarbon-constructed cascade intermediates possessing specifically located internal substituents or unsaturated centers, e.g., dialkylacetylenic moieties, set forth in the above-captioned patent to applicants (U.S. Pat. No. 5,154,853), those compounds disclosed by Moore and Xu,[19] that possess rigid polyalkyne spacers, or connectors, between branching centers and are thus prone to incomplete chemical transformations, and hence asymmetry, due to steric interactions, and those compounds set forth in the Tomalia patents set forth above which are amino-branched compounds having short linkages between branch points (thus minimizing void volume) and internal bridging trialkyl substituted nitrogen atoms possessing less than pure $sp^3$ hybridization, making internal nucleophilic substitution difficult.

Applicants have found[6] that the dialkylacetylene moieties of the cascade polymers set forth herein are also specifically located within accessible void regions. Applicants have shown that molecular guest probes, including diphenylhexatriene (DPH), phenol blue (PB), naphthalene, chlortetracycline (CTC), and pinacyanol chloride (PC) can be used as micellar probes to access the infrastructure of such cascade polymers utilizing known chemistry.[20-24]

Demonstrations of accessibility of void regions to chemical modification has led to the development of the ability to manipulate internal moieties within the spherically symmetrical dendritic macromolecule, after construction, to allow easy incorporation of internally located sensitive and/or reactive groups which otherwise would be difficult to introduce or protect during cascade construction. Specifically, the introduction of metal and metalloid centers at the interior of cascade infrastructures has been accomplished. Such derived compounds, referred to generically as metallospheres, superclusters, unimolecular Metallomicellanes and Nonmetallomicellanes, Metalloidomicellanes, derivatized Micellanes, or Micellanes, can be utilized for drug delivery of various metals and nonmetals, which are presently difficult to deliver in pharmacologically efficacious matters. The use of carrier-metal combinations as pharmacotherapeutic agents has had the problem of not being able to deliver sufficient metal/nonmetal to a site at a sufficiently low dose of the carrier of the metal/nonmetal per se.

For example, the U.S. Pat. No. 5,422,379 to applicants' provides a means of delivering high concentrations of the metal/nonmetal moiety(ies) to a site at a relatively low dose of carrier (Micellane system).

Accessibility to void regions can be achieved by various means. Accessibility can be achieved during synthesis of tiers of the macro-molecular or can be achieved after synthesis by various manipulations of the molecule. It has been found that these manipulations of the molecule can be achieved by increasing and then, decreasing the size of the molecule.

A further and most significant step has been taken towards specificity in the access of guest molecules to the void regions and binding of the guest therein. Specifically, a "lock and key" concept has been developed pertaining to unimolecular micelles which takes advantage of several demonstrated and unique characteristics of these cascade macromolecules. The advantageous characteristics include: (1) the internal, constructed, and predetermined or predesigned void domain(s) created within the micelle superstructure, (2) the ability to gain facile access to these inner void regions with molecular guest(s) to generate a micellar complex and possibly multimicellar complexes comprised of one or more hosts with one or more guests, (3) the ability to incorporate specific acceptor moieties into the structure of one or more arms, branches, or cascade building blocks or the synthetic activation of a dormant, or masked acceptor loci thereby affixing the acceptor moieties permanently, or for a controlled period of time, and (4) the unique homogenous structure and topology of the building blocks which allow the incorporation of predesigned acceptor moieties onto one or more of the unimolecular micelle branches. In other words, an acceptor region which will bind specifically to a complementary moiety can be engineered per se and then specifically disposed and preferentially exposed to the complementary moiety for irreversible or reversible binding thereto. Further, the micellar structure can contain an otherwise soluble receptor (acceptor region) and render the receptor soluble by virtue of soluble components on the micelle surface.

Utilizing these molecules, the present invention can provide for molecular recognition and binding in and between two or more micelles. This is specific binding of a key micelle with a lock micelle, the binding being selective as well as being able to be turned on and turned off.

SUMMARY OF THE INVENTION

In accordance with the present invention, there is provided a lock unimolecular micelle including at least one engineered acceptor for specifically binding a ligand thereto.

The present invention further provides a key micelle molecule comprising a core molecule and a plurality of branches extending therefrom. At least one of the branches includes a shank portion extending therefrom having a terminal moiety at the end thereof for binding to a complementary acceptor of a lock unimolecular micelle.

The present invention further provides a method of generating a unimolecular complex by combining a lock micelle molecule including at least one engineered acceptor within a solution containing the key micelle molecule and selectively binding the terminal moiety of the key micelle molecule to the acceptor of the lock micelle to selectively form a bimolecular complex.

In accordance with the present invention, there is provided a method of making a physicochemically operative monomer building block for synthesis of a cascade polymer including the steps of isolating a physicochemically operative moiety including an amino group and a multi-branched core alkyne building block including an amino group with bis(acid chloride) to form a physicochemically operative bis amide monomer including a physicochemically active portion and a branch portion.

The present invention further provides a monomer building block of the formulas

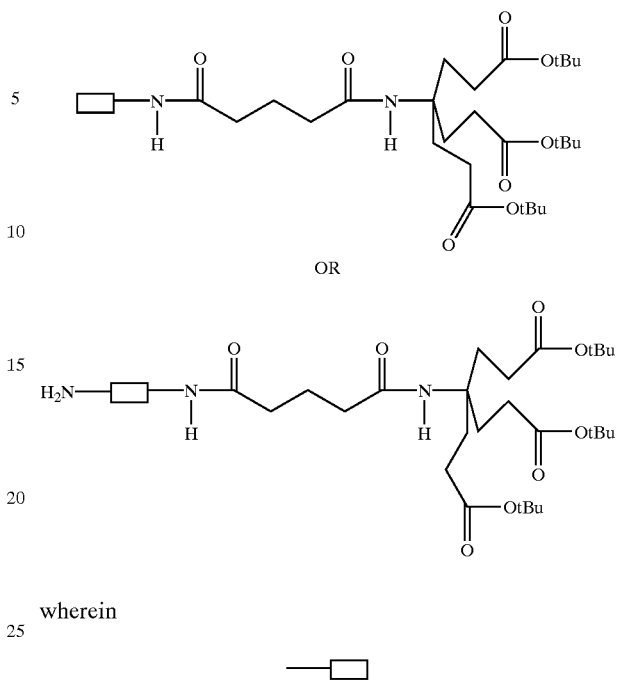

wherein is a physicochemically operative moiety.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1A:
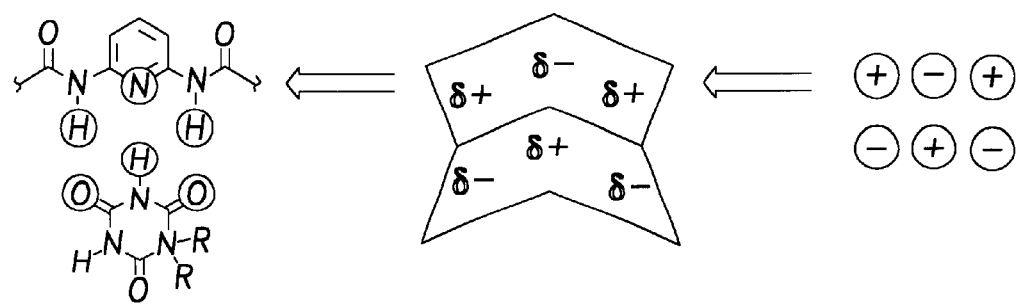
FIG. 1 shows some representative lock and key designs (column 1) and the concept of a specific key associating with a specific lock (column 2) (T. J. Murray, and S. C. Zimmerman J. Am. Chem. Soc. Vol 114., pp 4010–4011, 1992). The third column abstractly depicts the arrangement of partial positive and negative charges that are responsible for the molecular recognition inherent in the lock and key design. It should be noted that the lock and key concept is not limited to systems with three hydrogen bonds. The incorporation of sites in locks and keys that contain more or less donor/acceptor sites is envisioned.

The present invention provides a lock and a key unimolecular micelle. The lock unimolecular micelle includes at least one engineered acceptor for specifically binding a ligand, such as a key unimolecular micelle thereto.

The term "lock micelle" means a unimolecular micelle including an acceptor region for specifically binding, with a predetermined affinity to a specific complimentary site of a ligand, the acceptor being disposed within an engineered void region of the micelle which further defines a pocket which allows entrance thereto of the same specific ligand, based on the ligands secondary and tertiary structure.

The term "key micelle" refers to specific ligands which are engineered micelles having the binding region which is complimentary to the aforementioned receptor (acceptor region) and a secondary and tertiary structure allowing entrance thereof with the void region of the lock micelle containing the receptor.

Thus the lock and key concept requires a combination of access of the key micelle region including the binding area into the void region of the lock micelle, and then affinity of the acceptor region to the binding region of the key micelle. This allows for competitive binding between key micelles for a receptor, as well as with naturally occurring ligands, such as drugs, or the like, for the acceptor. It also allows for competitive binding between the lock micelle and natural receptors for specific drug as the binding region, such as a barbiturate, and release the drug bound key micelle at a naturally occurring receptor having a higher affinity therefore in an equilibrium environment.

More specifically referring to the micellar structure, the present invention provides a unimolecular micelle including internal void areas, the void areas including reactive sites capable of covalent and noncovalent bonding to guest(s). The unimolecular micelles of the present invention are cascade polymers which act as micelles. Such unimolecular micelles can be generally in the form of those disclosed in U.S. Pat. No. 5,154,853 to applicants, cited above, being all alkyl molecules, or in the form of those disclosed in the Tomalia patents discussed above, having a nitrogen core or branching site. Such compounds have pre-defined branching, depending upon the number of sequential tier additions that are performed in accordance with the above-cited references. The etymology of the term "Micelle", as employed in the classical or usual sense, refers to a noncovalently associated collection (aggregate) of many simple molecules functioning as a unit having unique properties (e.g., aqueous solubilization of water insoluble materials) that are not observed with the individual molecules which comprise the micelle; whereas as used herein, unimolecular micelle or micellane refers to a single macromolecule, possessing a covalently constructed superstructure, that can perform the same function(s)[6] as a classical micelle. Additions to these terms denote the incorporation of specific types of metals or nonmetals within the chemically accessible lipophilic interior of the unimolecular micelle. The term ligand is meant to describe any site that has the ability to donate electron density, such as a pair of electrons to a metal or nonmetal moiety, thus forming a covalent or noncovalent bond. Most often the term is used when discussing metals that are bonded, or complexed, to atoms, such as N, P, O, and/or S. The term guest(s) is (are) meant to describe any metal or nonmetal (or any reasonable combination thereof) specie(s) that can be introduced into or onto the cascade framework. The introduction can be irreversible due to the formation of covalent bonds or reversible due to the formation of noncovalent bonds that are easily broken (e.g., hydrogen bonds) or the reversibility may be due to lipophilic-lipophilic and hydrophilic-hydrophilic attractions.

Micelles made in accordance with the present invention can be described as having at least one core atom, preferably a carbon atom, and arms branching from the core atom. At least one acceptor is an integral part of at least one of the branches for binding at least a portion of the ligand within the void region. At least some of the branches can extend about the acceptor defining a predetermined pocket containing the void region. Accordingly, the pocket is a lipophilic container of the void region and acceptor and defines an opening to the exterior of the micelle from the void region. That is, the branches form a lipophilic wall of a cave in which the acceptor is exposed. Such a pocket can be engineered to include one or more acceptor sites as described below. Further, the acceptor sites an be engineered into any branching tier or tiers as needed to engineer a specifically defined receptor or docking site which is complementary to the tertiary and quartenary structure of the ligand to be bound. As it will be described below, the ligand can be in the form of a specifically engineered key micelle such that the key inserts into the pocket and includes a terminal moiety which binds specifically to the acceptor site(s).

The unimolecular micelle or "void domain", a three dimensional entity, is critical to this lock and key concept in that it can essentially be considered a tertiary structure of the unimolecular micelle system. Since all aspects of the micellar species can be predetermined and deliberately designed or engineered, the sum of the "void regions" or total void domain of the macro-molecule is a designed parameter contained in dendritic building blocks or the activated armed site(s) for molecular attachment of the complementary ligand or key unimolecular micellar molecule. Hence, the monomers, or building blocks that eventually comprise the resulting unimolecular micelle in still (1) a primary structure (attributed to nuclei-connectivity), (2) a secondary structure (attributed to fundamental nuclei interactions such as hydrogen binding, dipole interactions, and London forces), (3) a tertiary structure than can assume molecular shapes such as ribbons, zippers, threads, and spheres (internal and external confirmations induced by secondary structure), and (4) a dynamic, structured void domain or "quasi-tertiary" structure of the unimolecular micelle determined by the combination of the primary, secondary, and tertiary structures. The quasi-tertiary domain comprises one of the major domains of the micellar macro-molecular structure which includes the immediate region above the micellar surface, the micellar per se, and micellar framework. All of these domains are active in that they can be used to effect chemical and physical changes of the unimolecular micelle, its environment, a molecular guest or guests, or any of the cited combinations.

The terminations of the arms or with larger branching, possibly mid-portions of the arms may fold to form an outer surface of the micelle. The surface of the micelle is exposed to immediately surrounding environment in which the micelle is disposed. This environment will have a certain hydrodynamic character, determined by properties such as pH, lipophilicity-hydrophilicity characteristics. Such surface characteristics also lead to general solubility of the micelle, even when carrying a relatively insoluble guest therein.

The surfaces of the micelles can be readily coated with metal ions. Mono-, di-, and trivalent metals are being possibly bonded directly or indirectly through terminal carboxyl groups or the like, similar to the dissolution of metal ions by most micellar or acidic systems. Likewise, the surface of the micelle can include polar, nonpolar, and/or hydrodynamic group sensitive to pH, ionic or other hydrodynamic changes. The method of making such micelles are disclosed in "Macromolecules" vol 27, no 13, 1994, pp. 3464–3472.

The micelles can be characterized as having branches or arms which can be flexible, each of the arms terminating with a hydrodynamic reactive group. The term "flexible" means that the arms are capable of extending away from and then, in reverse, folding towards the core atom. Flexibility further describes the relative ability of these arms to extend and contract relative to the core atom. Thusly, as discussed below, the branches or arms can be chemically altered such that the arms or branches can extend further or shorter from the core atom thereby controlling the ability of the micelles to expand in a given environment having no hydrodynamic characteristics. In combination with the flexibility of the arms or branches, the nature of the terminal groups can also effect the expansion of the micelle in different environments. Thusly, the selection of specific hydrodynamic reactive groups can effect the relative expansion and contraction of the hydrodynamic radius of these molecules.

The term "hydrodynamic reactive group" refers to chemical groups which can be bound to the terminal ends of arms or branches which are reactive with outer environment based on the hydrodynamic character of the environment. For example, groups such as alcohols, amines, carboxyls, thiols, phosphines, ammonium ions, sulfoniums ions, phosphonium ions, nitrates, sulfates, phosphates, and carboxylates, as well as other known reactive groups can be modified depending upon the hydrodynamic character of the surrounding environment. For example, hydrodynamic changes such as pH can proteinate and diproteinate carboxyls and amines and thereby change the solubility characteristics of these reactive groups in the environment. Increased solubility in combination with flexibility of the arms or branches of the micelle will result in expansion of the arms and the concomitant effective increase in hydrodynamic radius of the micelle. Essentially, the molecule becomes larger. Decreases in the solubility will likewise contract the molecule.

It has been found that with significant increases in length of branches or arms, the arms or branches may fold into the micelle thereby not necessarily exposing the terminal end of the arm or branch but rather, a mid-section. Accordingly, hydrodynamic groups exposed in this manner can also effect expansion and contraction of the micelle. The above description of expansion and contraction in response to changes in the environment related to the solubility of the branching of the micelle is further described in U.S. Pat. No. 5,422,379 to applicants', assigned to the assignee of the present invention.

Figure 11:
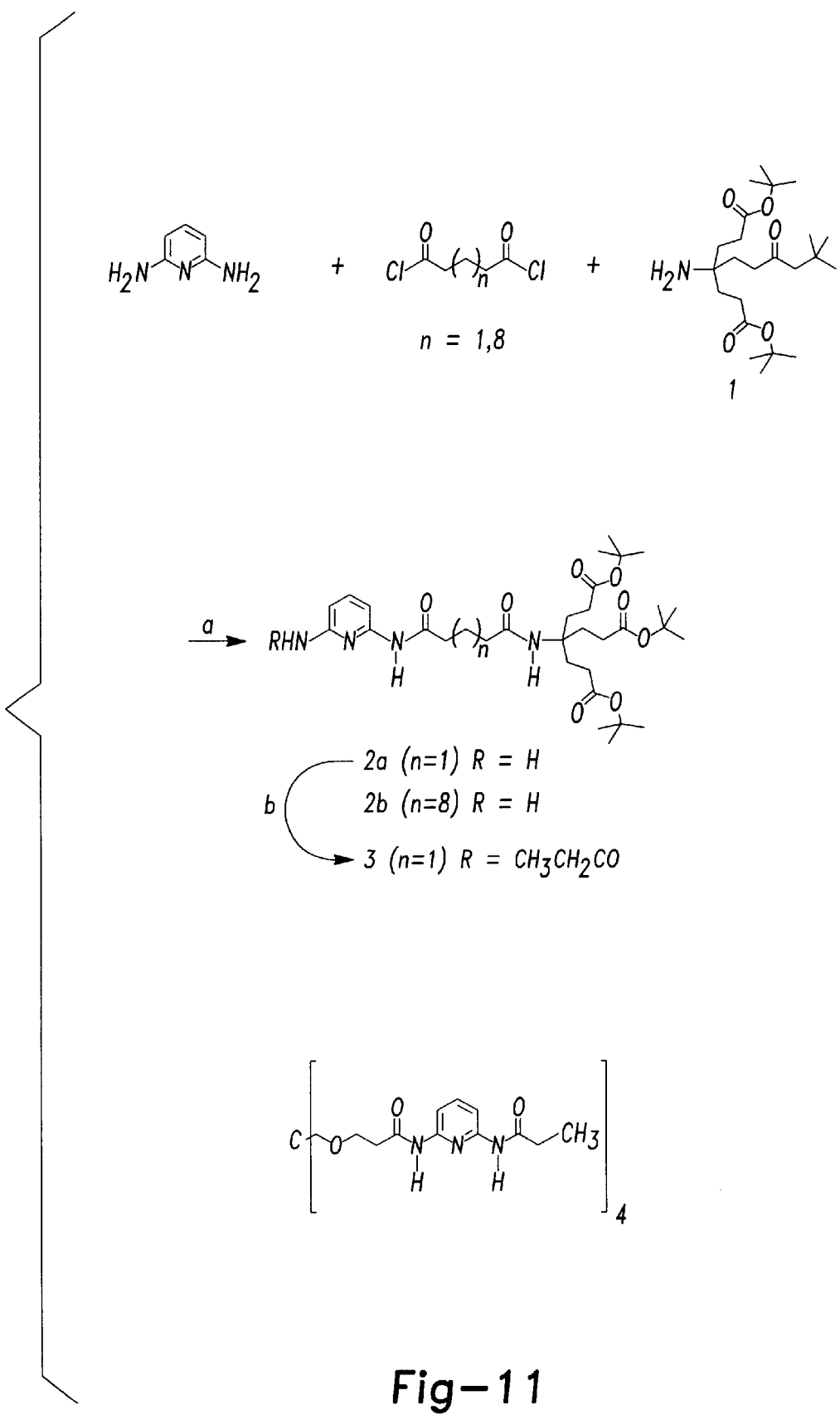
FIG. 11 shows a three-component reaction for the preparation of building blocks possessing a H-bonding, molecular recognition site, wherein the reagents are THF, Et(i-Pr)$_2$N, 0–25° C., 24 hours.

The micelles of the present invention can be engineered so that the expansion of the micelle exposes the opening of the pockets thereby allowing for exposure of the opening of the pocket to ligands disposed in the environment and binding of the acceptor to a complementary moiety. Contraction of the micelle can fold the branches over the opening of the pocket thereby shielding or masking the void area and acceptor (FIG. 11). Accordingly, the environment of the micelles can be manipulated to turn on or turn off accessibility to binding of the locked micelles with ligands such as key micellar molecules described below.

For example, pH, immiscibility or other factors described in the above mentioned patent application U.S. Pat. No. 5,422,379 to applicants' can be utilized. For example, an aqueous solution of an acid terminated lock micelle at pH≧7 would be in an extended (open or porous) configuration. Substrate (guest) molecules are readily encapsulated (dissolved) within the lipophilic micelle interior; lowering the solution pH (<4) will collapse the lock micelle (close the pores) and entrap the key (guest) molecule. This lock-key (host-guest) complex can be isolated from the solution via filtration methods (such as, dialysis, ultrafiltration, or gel permeation). Dissolution of the isolated lock-key complex in a solution with pH≧7 will facilitate the release of the entraped key molecule. The lock micelle imparts its solubility characteristics onto the entraped key molecule and should serve as a protective "sheath", which can protect labile functionalities on the key molecule.

It should be noted that the U.S. Pat. No. 5,154,853 to applicants and assigned to the assignee of the present invention (1992) discloses that unimolecular micelles made in accordance with the present invention have a porosity which is pre-determined, created by the relationships of the branches, the core defined above, and each of the quaternary areas or tertiary centers (carbon core or nitrogen branching sites, respectively) and created by each additional tier layered thereon. The porosity of the inside core can be changed by is increasing or decreasing the distances between the quaternary or tertiary centers; that is, by changing the branch arm lengths. Hence, pursuant to known art developed by applicants, the micelles of the present invention can have specifically engineered aspects of size, porosity, outer surface and internal binding sites.

As discussed above, the surface character of the micelles made in accordance with the present invention can be varied. For example, a carboxyl surface can be created, thereby rendering the micelles useful for detergents and surfactants, and also reactive to pH.[25] Changes in pH which increase the solubility of the surface components can expand the dendritic arms, thereby allowing accessibility to the void regions of the unimolecular micelle. Returning the pH to its original character can then contract the dendritic arms, thereby once again enclosing the void regions. This method of changing solubility of the unimolecular micelles by changing the environment in which the unimolecular micelles are retained can be used to provide accessibility to the void regions for chemical modification, as discussed in detail below.

Besides carboxyl groups, hydroxyl groups, and amines, other acidic, neutral, and/or basic functionalities can be incorporated onto the surface or on interior dendritic arms adjacent to the void regions of these unimolecular micelles as set forth in U.S. Pat. No. 5,154,853. The void areas of these unimolecular micelles made in accordance with the present invention have been characterized. The expanded and contracted nature of such dendritic arms defining the micelles have also been characterized. U.S. Pat. No. 5,422,379 to applicants' discloses various structures capable of expansioning contraction for exposure of void regions and masking of void regions which can be utilized for masking and shielding the opening to the pockets of the micelles made in accordance with the present invention, and are incorporated herein by reference.

The branches of the lock micelle can include terminal moieties as described above. The pockets defining the void regions can include what are termed "gatekeeper" molecules for allowing the entrance of only specifically structured molecules into the opening of the pocket. That is, particular molecules can be engineered at the opening of the pocket for the external environment defining the void region which are chemically selective for particular ligands (and specifically key micelle molecules as described below) for entrance into the opening of the pocket.

For example, the gatekeeper molecules can be selected from the group including, but not limited to, amino acids (such as tryptophan, phenylalanine), carbohydrates and sugars, charged or ionizable groups (including carboxyls, amines, sulfonic acids), metalchelators (including pyridine, phenanthroline, crown ethers, azacrowns), and host moieties such as β-cyclodextrin. A particularly useful example is a gatekeeper moiety which is a chiral molecule for favoring a single enantiomer of a guest molecule which can enter the opening of the pocket to bind the acceptor. Accordingly, the present invention can be utilized as a filtering mechanism for removing a specific enatomer of a molecule from a solution.

For example, a lock micelle having an R or S configuration can be used as either a soluble form or insoluble form bound to a matrix. Tryptophan is an example of a chiral molecule which can terminate a dendritic macro-molecule as disclosed in the paper entitled "Polytryptophane Terminated Dendritic Molecules", Newkome et al. *Tetrahedron Asymetry* Vol 2., No. 10, pp. 957–960, 1991, incorporated herein by reference. Chiral gatekeeper molecules will allow binding of only one of the oppositely active components of a racemic mixture. Accordingly, pursuant to drug industry standards regarding separation of enantiomers (an active drug component from an inactive drug component) the present invention can be used as a filtering system. For example, an aqueous solution of the acid terminated chiral lock micelle at pH≧7 would be in an extended (open) configuration. Upon addition of a racemic mixture of a complimentary key, only one enantiomer will interact with the lock micelle. Lowering the solution pH (<4), will collapse the lock micelle and entrap the preferentially complexed chiral key molecule. This chiral lock-key complex can be separated from the solution via filtration methods (such as, dialysis or ultrafiltration), removing the remainder of the racemic mixture and other impurities. Dissolution of the isolated chiral lock-key complex in a solution with pH≧7 will facilitate the release of the chiral key molecule.

The acceptor is a moiety having a binding region complementary to a desired binding region of a ligand. The combination of an acceptor with an engineered pocket having an opening including gatekeeper molecules as discussed above provides a unique family of lock micelle molecules wherein one ligand (molecule) fits the cavity or structural shape of a second ligand, such as in a host-guest relationship or nonchemically as a hand in a glove. The structural relationship has a complementary order necessary for a docking of one to the other, or molecular complexation.

The structural incorporation of a molecular complimentary binding region into the arms of a cascade macromolecule via synthetic procedures generates a molecular lock which is then capable of docking, or complexing, with a specific family of molecular complimentary key materials. The molecular recognition of this key/lock combination permits the molecular incorporation of guest molecules in specific locus or locii permitting an approach to molecular inclusion and encapsulation in a transport domain insulated, for the most part, from the environment outside of the cascade (dendritic) macromolecule. Thusly, relatively insoluble or enzyme degradable molecules can retain their bioactivity while being shielded within the micellar lock and key domain. Upon reaching a binding site having a higher affinity for the guest including at acceptor region, the guest is released and combined at the receptor. Hence, the present invention provides a guest delivery system.

Figure 1B:
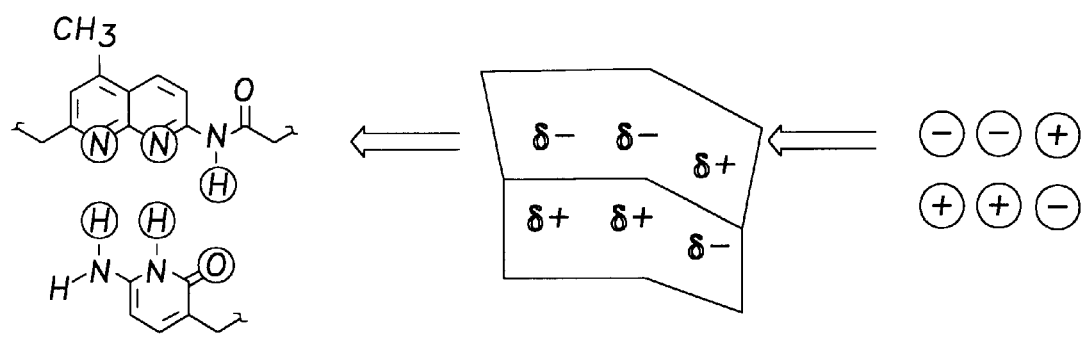
Figure 1C:
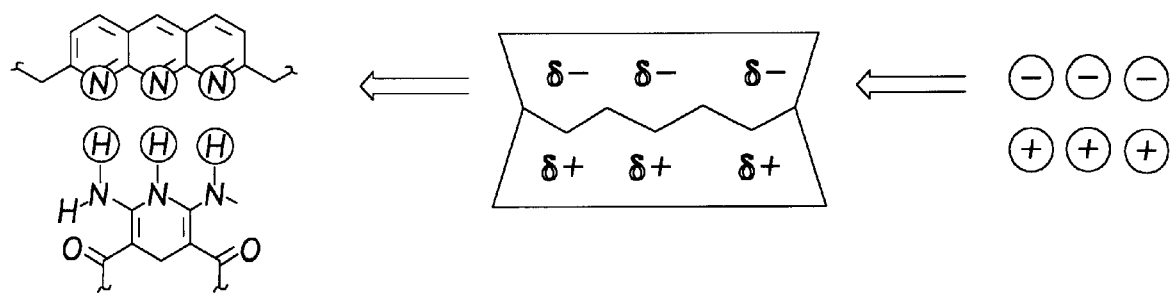

FIG. 1 provides several examples of the general concept of an acceptor-ligand complimentary relationship. The relationship is not limited to complimentary units that possess 3 H-bonds, but rather it may be applied to to donor/acceptor units that are based on one or more H-bonds.

In view of the above, the acceptor as a moiety selected from a group consisting essentially or partially charged molecules engineered to be complimentary to a binding portion of a guest molecule. The acceptor can be either partially negative, partially positively charge. Specifically, the acceptor can be selected from the group consisting of essentially partially charged molecules engineered to be complimentary to a binding portion of the guest molecule. The acceptor can include at least one partially negative charge, one partially positive charge or a combination thereof. Specifically, the acceptor can be selected from group including bipyridines, tripyridines, and poly Lewis base moieties comprised of oxygen, nitrogen, sulfur, phosphorous, halides, or transition metals with a donor pair of electrons.

The opening of the pocket is predetermined distance from the acceptor for defining a specific depth that key micelle can be inserted into the pocket to allow only binding of specific key micelles. Again, this adds to the "combination" of the lock for specifying key molecules of a predetermined secondary and tertiary structure.

Figure 2:
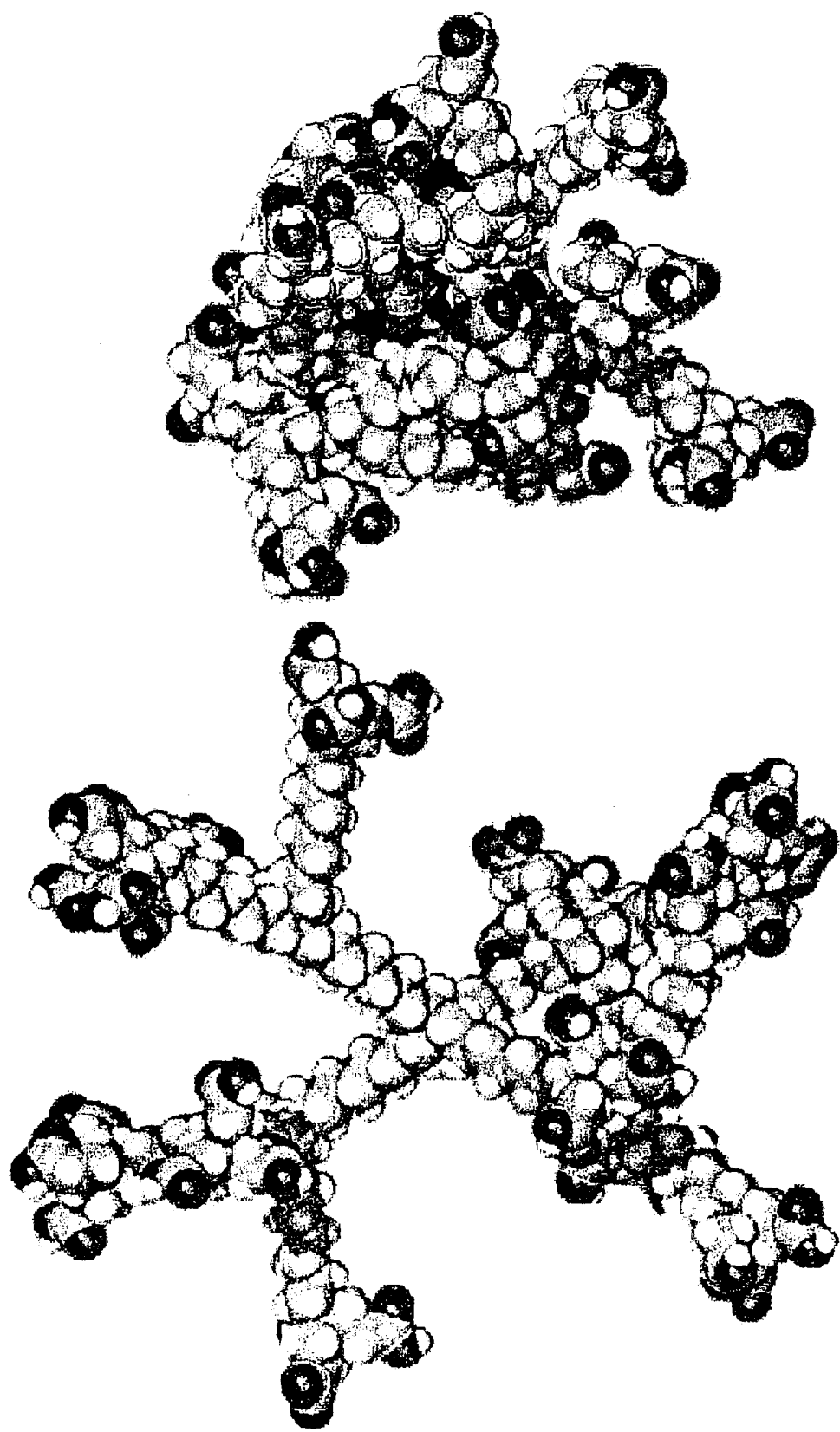
FIG. 2 shows a space filling model of a hydrocarbon based cascade macromolecule in the expanded and contracted form. In the expanded view, the interior core is clearly visible, whereas, in the contracted conformation the central core is obscured from view and hence much more protected from the environment than when it is expanded.
Figure 3A:
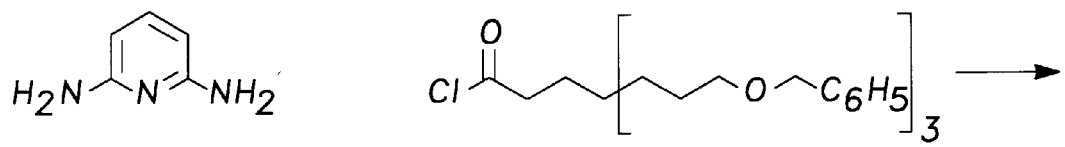
FIG. 3 illustrates the use of hydrocarbon-based building blocks, such as the acid chloride tris(benzyl ether), for the construction of four-directional dendritic macromolecules. The use of standard amine-acid chloride chemistry allows the introduction of the diaminopyridine acceptor unit (A) into the cascade framework.
Figure 3B:
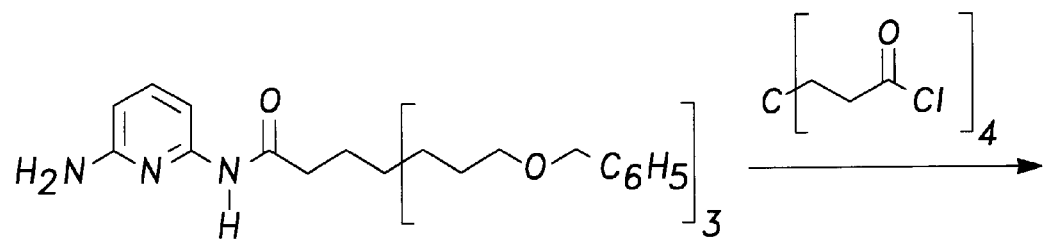
Figure 3C:
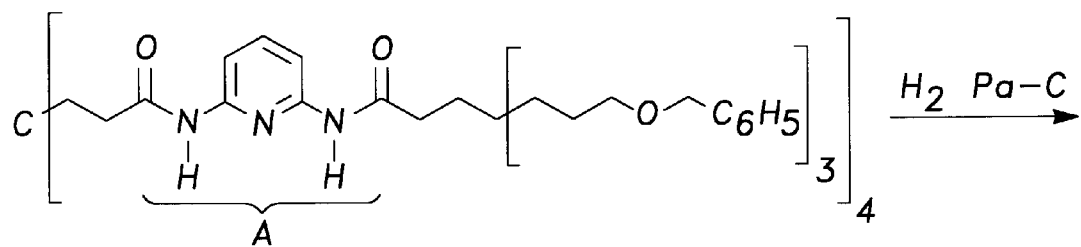
Figure 3D:
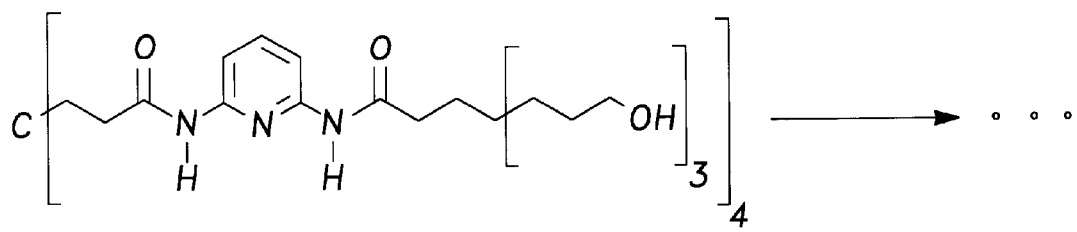

A key micelle molecule comprises a core molecule and a plurality of branches extending therefrom a predetermined distance and at least one of the branches including a shank portion extending therefrom having a terminal moiety at an end thereof for binding to a complimentary acceptor of a lock unimolecular micelle. Such a shank portion can consist essentially of a multicarbon chain, the multicarbon chain including zero to 22 carbon atoms. Of course, such a shank portion can be made by various molecular mechanisms known in the art. But it must provide a spacing allowing access of a terminal binding region to an acceptor region within a pocket of a micelle. Examples of such key micelles or molecules are shown in FIG. 2.

The terminal moiety of the key micellar molecule includes the tertiary structure including at least one partially charged portion, either negative or positive or a combination of the two. Such terminal moieties can be selected from the group including barbiturates, such as Allobarbitol, Aminoglulehimide, Amobarbitol, Barbituric acid, Barbital, Bemgride, 6-Azauridine, Phenobarbitol, Primidone, Secobarbital, Pentobarbitol, Diazepam, Flurazepam, Methaqualone, Meprobamate, and also carbohydrates, such as sucrose, alditols, mannitols, hexoses and amino acids and peptides such as trytophane, phenylalanine, glycine and nucleotides and nucleosides such as purines and Pyrimidines, guanine, cytosine, thiamine, and adenine. As discussed above, the terminal moiety can be chiral.

An advantage of utilizing the present invention is where the terminal moiety is insoluble in water. The branches of the micelles can include water soluble moieties bound thereto for rendering the micelle water soluble. Polarizable groups are water-soluble and when complexed to a donor/acceptor moiety they possess the potential to make the compliment water-soluble.

Initial design of this concept, introduces a 2,6-di (acylamino) pyridine moiety (A) as the "acceptor unit" in the cylinder lock. Such incorporation is depicted in FIG. 3.

Figure 4A:
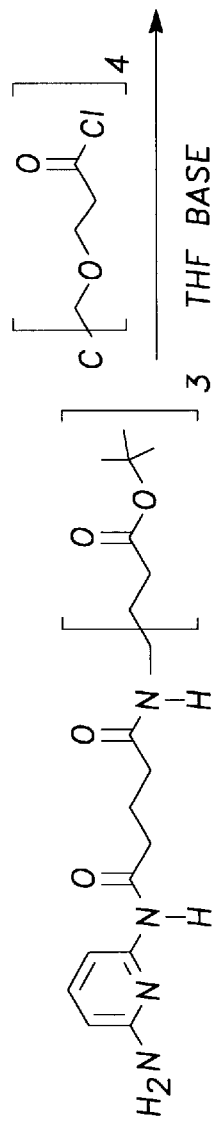
FIG. 4 depicts a versatile method for the construction of four-directional cascade locks containing four diaminopyridine units (A) equidistant from the central core (II and III). The aminopyridinetriester building block used for the construction of the dendritic arms is prepared via high dilution methodology that allows the incorporation of various alkyl chain lengths separating the triester and aminopyridine moieties. This feature allows the design of building blocks that introduce varying degrees of lipophilicity to the interior cascade superstructure. Standard formic acid mediated tert-butyl ester conversion to acid functionalities allows the formation of water-soluble locks as well as generates the poly(acid) precursor for the addition of another tier, or layer, of cascade building block [in the depicted case, the aminotris (tert-butyl ester)] via standard peptide-type coupling conditions. It should be noted however that other amino/ester building blocks can be added to the poly(acids), such as the previously described aminopyridinetriester, via the same technology.
Figure 4B:
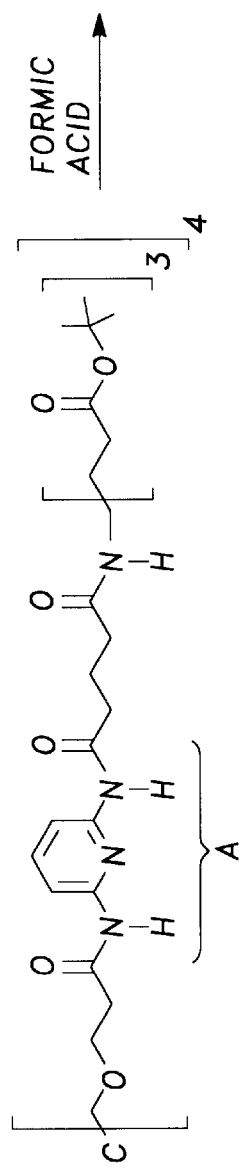
Figure 4C:
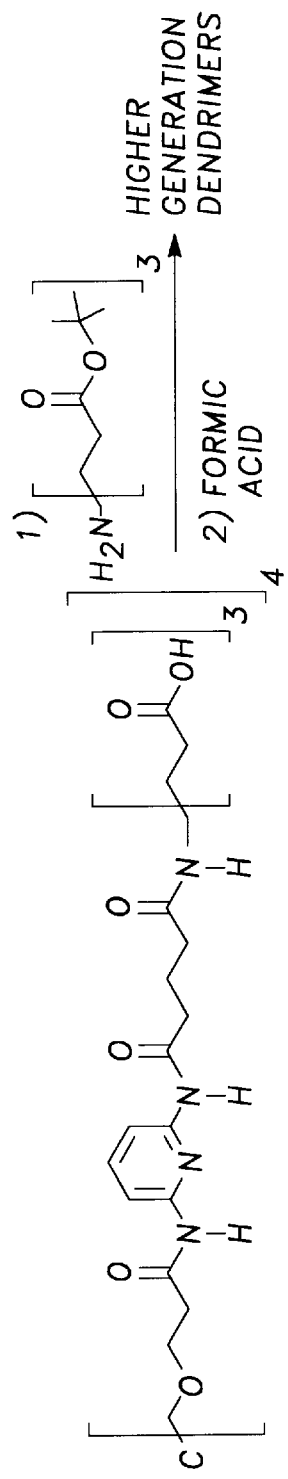

Based on applicants' all-carbon unimolecular micelle model, the acetylene moiety is replaced by the appropriate (poly) functionality. Alternate and more simplified incorporation can be envisioned in FIG. 4, utilizing other related dendrons, or cascade building blocks, (specifically, the aminotris(tert-butyl ester)) previously described in the applicants' patent application U.S. Pat. No. 5,422,379 to applicants' for the said dendritic building block. Such a process incorporates the acceptor units(s) in the lock; however, the processes herein described are not limited to only the first tier of construction with four binding loci (as depicted in FIG. 4), but can be incorporated at higher generations using known chemistry.

Figure 5A:
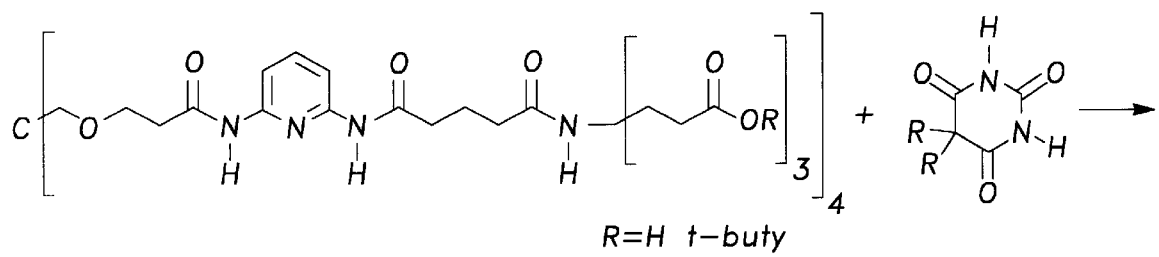
FIG. 5 illustrates the docking motif of the lock (III) and the bit portion of a generalized key. In this case, the bit (IV) is constructed of barbituric acid or any derivative thereof. Since there are four diaminopyridine units incorporated into the dendritic structure, up to four equivalents of key can be constrained to the cascade framework (V).
Figure 5B:
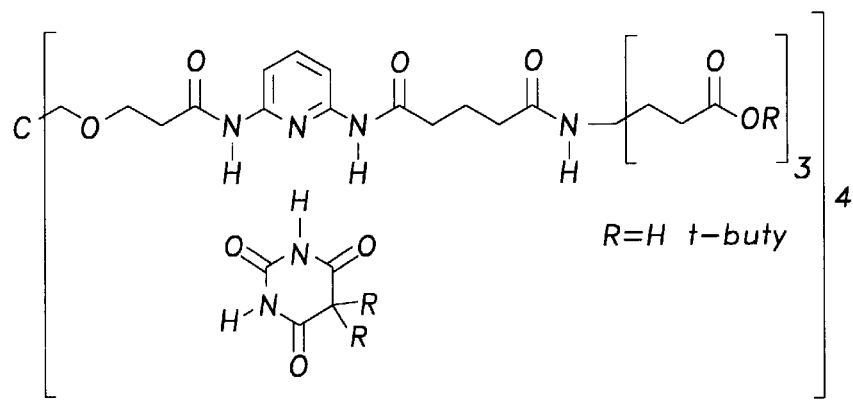

Initial design of the key utilizes the complementary nature of A, thus an imide (CONHCO) moiety fits the model. The case of barbituric acid (IV) was initially used as an example to is evaluate this complimentary relationship. Barbituric Acid and related materials are depicted in FIG. 5.

Figure 6A:
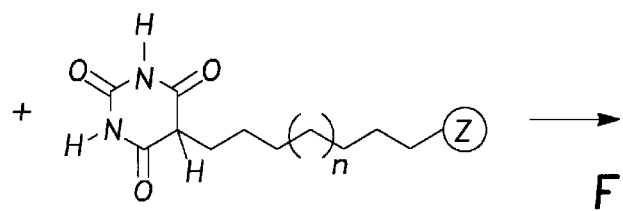
FIG. 6 shows the lock and key motif (V) whereby the bit of the key is connected to a "shank" (in this case depicted as a hydrocarbon chain) which is further connected to a "bow" or "head" (Z) of the key. Z can be envisioned as being any group or functionality that can logically connected to the bit through the shank. This can include another cascade structure that can be designed to enhance (or hinder) aqueous (or organic) solubility.
Figure 6B:
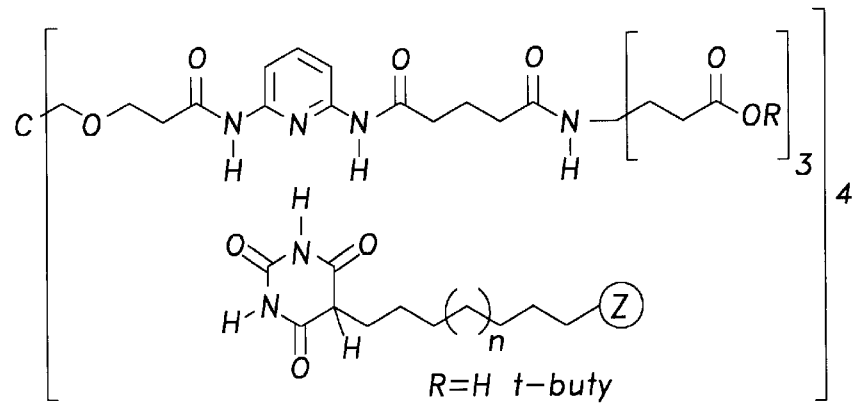

To illustrate the key/lock principle, four equivalents of the key are added to the dendritic macromolecule possessing the four lock locii. Each key fits the lock perfectly, resulting in the molecular incorporation of four specific guest molecules within the void domain of the macromolecule (FIG. 5). Proof of this concept is by standard spectroscopic procedures. The introduction of other keys possessing the same complimentary portion but different shaped handles on the "bit" region of the key has been shown to give analogous inclusioned and docked guest within the lock structure. FIG. 6 shows other related examples in order to establish the facile ability to molecularly secure reagents within the cavities of these spherical polymers. The use of different attachments (Z; FIG. 6) to the barbiturate's unique "bit" region, via an appropriate connector moiety such as an alkyl chain, permits the molecular entrapment of diverse materials within the lipophilic core of these precursors to the water-soluble spheres or the water-soluble unimolecular-micelles. hydrolysis of the lipophilic macromolecules, e.g. II, to the hydrophilic counterparts does not alter the docking region within the core. Treatment of III (R=H) which can be obtained by simply the hydrolysis of V (R-tbu). Either route gives rise to a water soluble material processing the inclusioned (locked) guest (key).

Figure 7A:
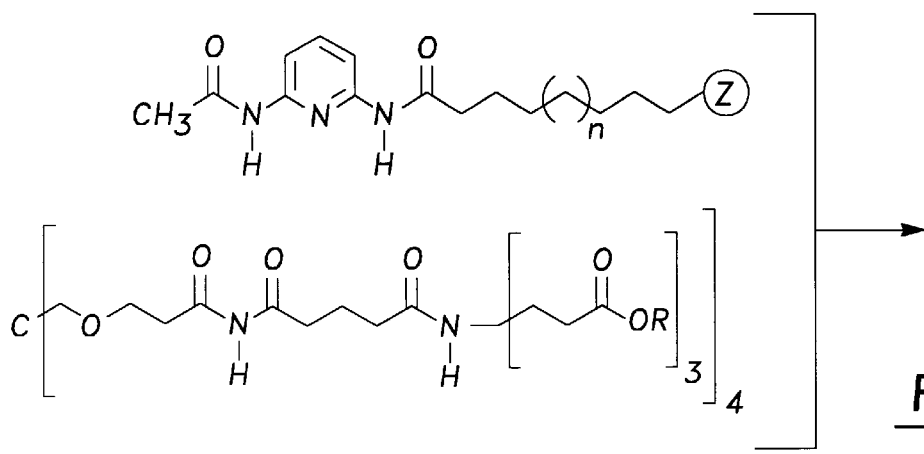
FIG. 7 demonstrates some of the versatility and latitude in designing cascade "locks and keys" in that the donor/acceptor moieties may easily be reversed. However, the hydrogen bonding that results from the lock and key connectivity is the same and is based on similar molecular recognition.
Figure 7B:
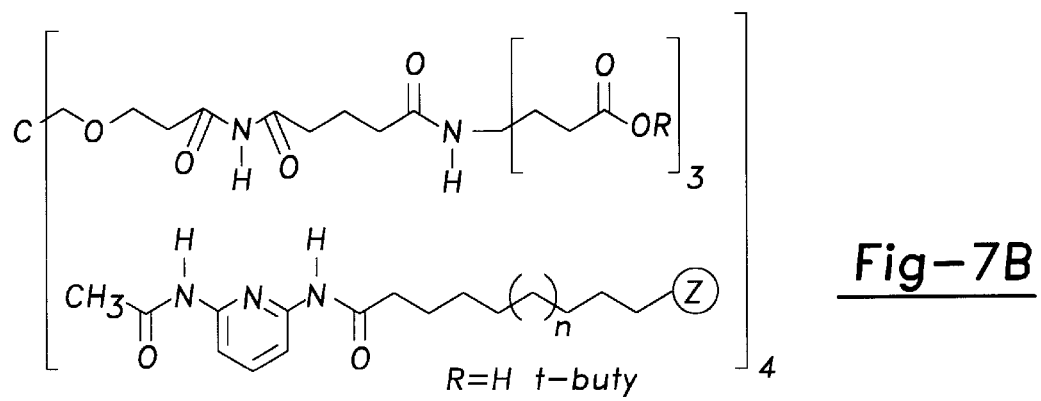

The key/lock relationship can be engineered to almost any complimentary set of organic binding sites. Thus, the complimentary regions can be interchanged, which is depicted in FIG. 7. Here the inside moiety (CONHCO) is incorporated in the "lock's cylinder". The key now possesses the di(acylamino)pyridine portion in the unique "bit" region. The molecular recognition by the formation of three-hydrogen bonds is similar to the process described in FIGS. 5 and 6.

FIG. 1 illustrates the other possible arrangements of "three pin lock cylinders" (i.e., the physical juxtaposition of hydrogen-bond donor and hydrogen-bond acceptor moieties. Column 1 lists representative examples of locks and keys; column 2 pictorially shows the molecular recognition of the locks and keys as being highly specific due to the precise positioning of partial positive and partial negative charges inherent in the molecular receptors and donors; column 3 depicts the possible electrostatic groupings for a three H-bond lock and key. The lock and key concept for unimolecular micelles is not limited to three H-bond locks and keys. Similar complimentary components complexed via 1, 2, (or more) H-bonds can be envisioned and incorporated into the cascade, or dendritic superstructure.

Alternative keys can use other molecular recognition techniques other than hydrogen bonding. The use of metal or several metal center(s) can be employed in which selective bonding can be shown. FIG. 8 shows the simplest of complex modes in which the lock and key both possess a terpyridine moiety. The key is converted to the Ru(III) complex, which can be introduced to the lock generating the Ru(II) bis-terpyridine complex in very high yields. Other metals such as Co(II), Fe(III), Os(II), etc. work equally well.

Figure 9A:
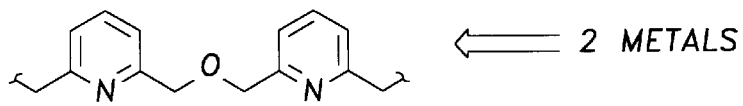
FIG. 9 illustrates the potential to incorporate multiple donor/acceptor sites onto a branch(s) of the cascade superstructure.
Figure 9B:
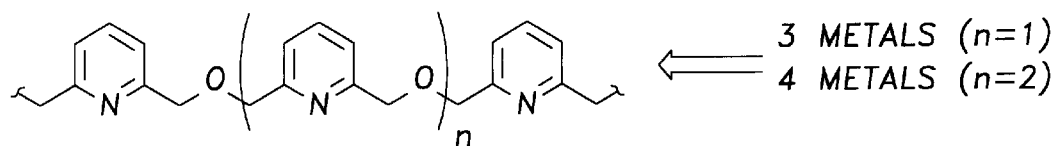
Figure 8A:
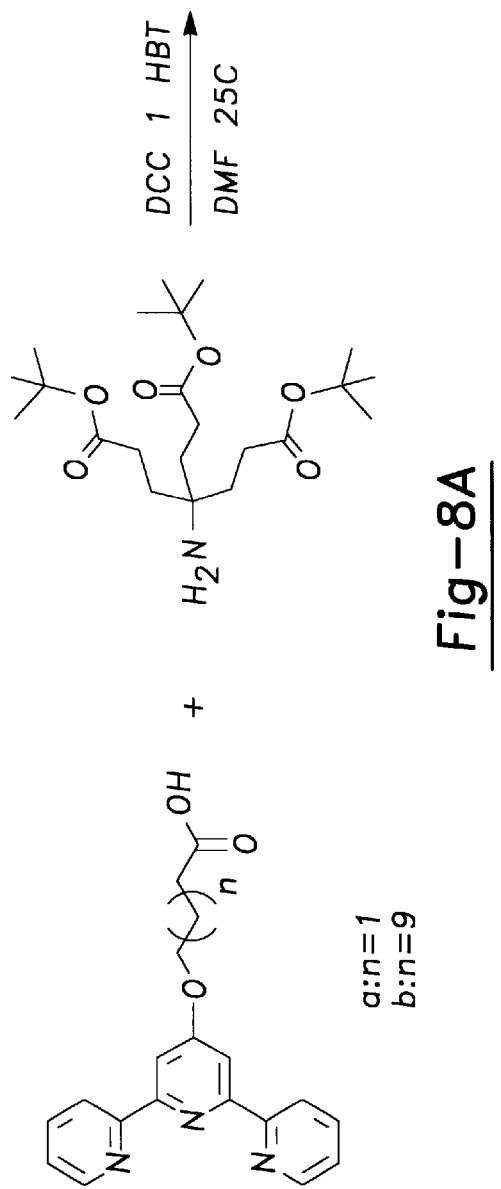
FIG. 8 illustrates the construction of locks and keys based on covalent metal-ligand bonding. As depicted, one lock site can be attached to a growing cascade structure via the connection of a terpyridine moiety to a carboxylic acid which can then be subjected to the standard amide coupling and ester deprotection methods that have been previously described.
Figure 8B:
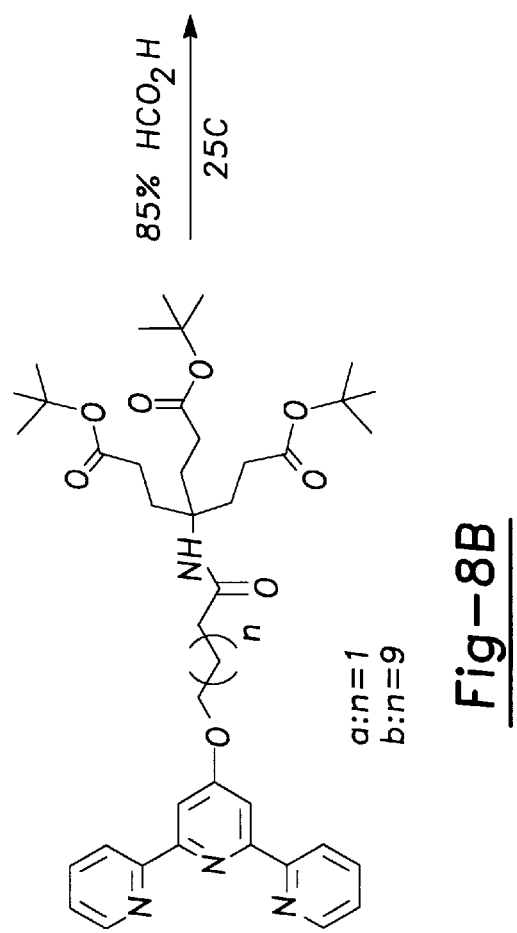
Figure 8C:
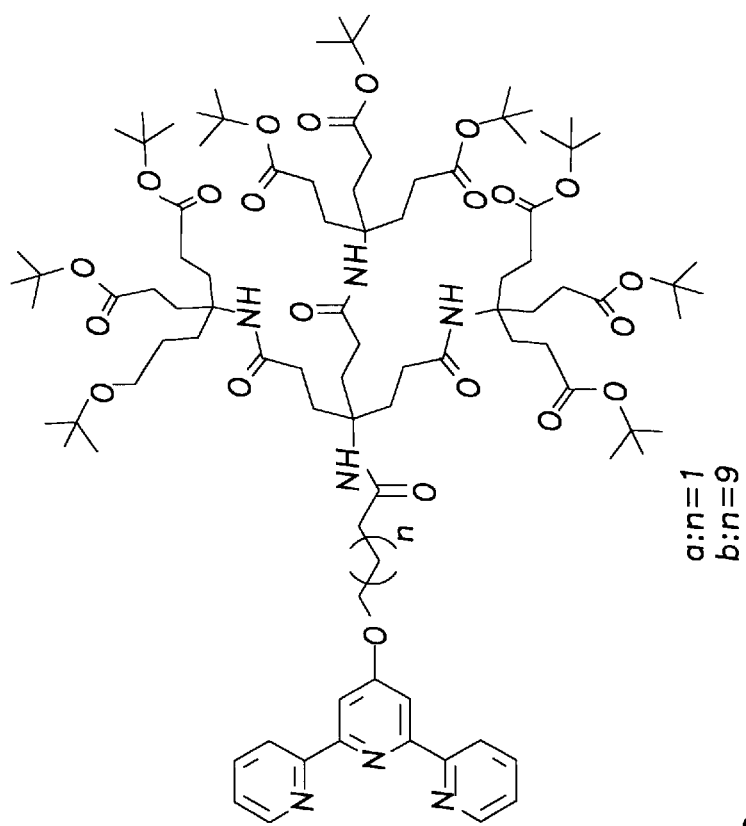
Figure 8C:
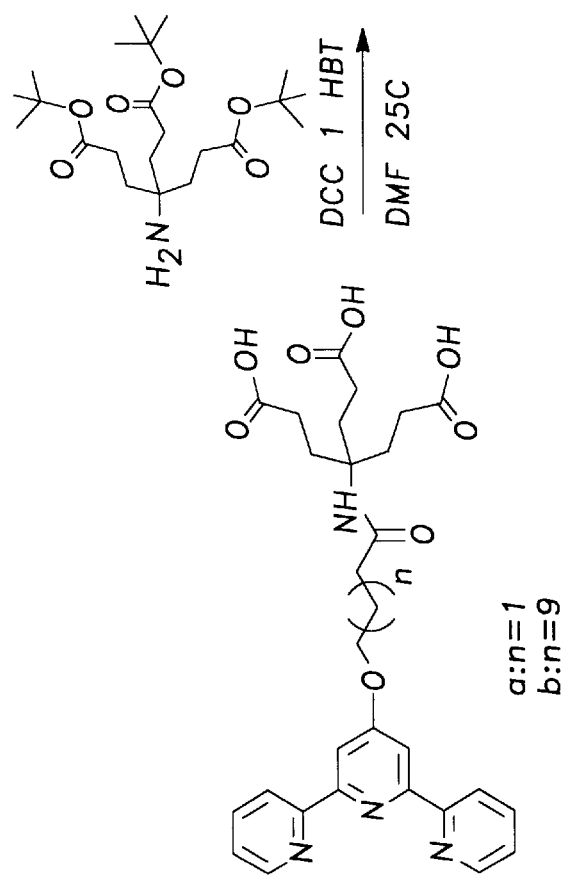
Figure 10:
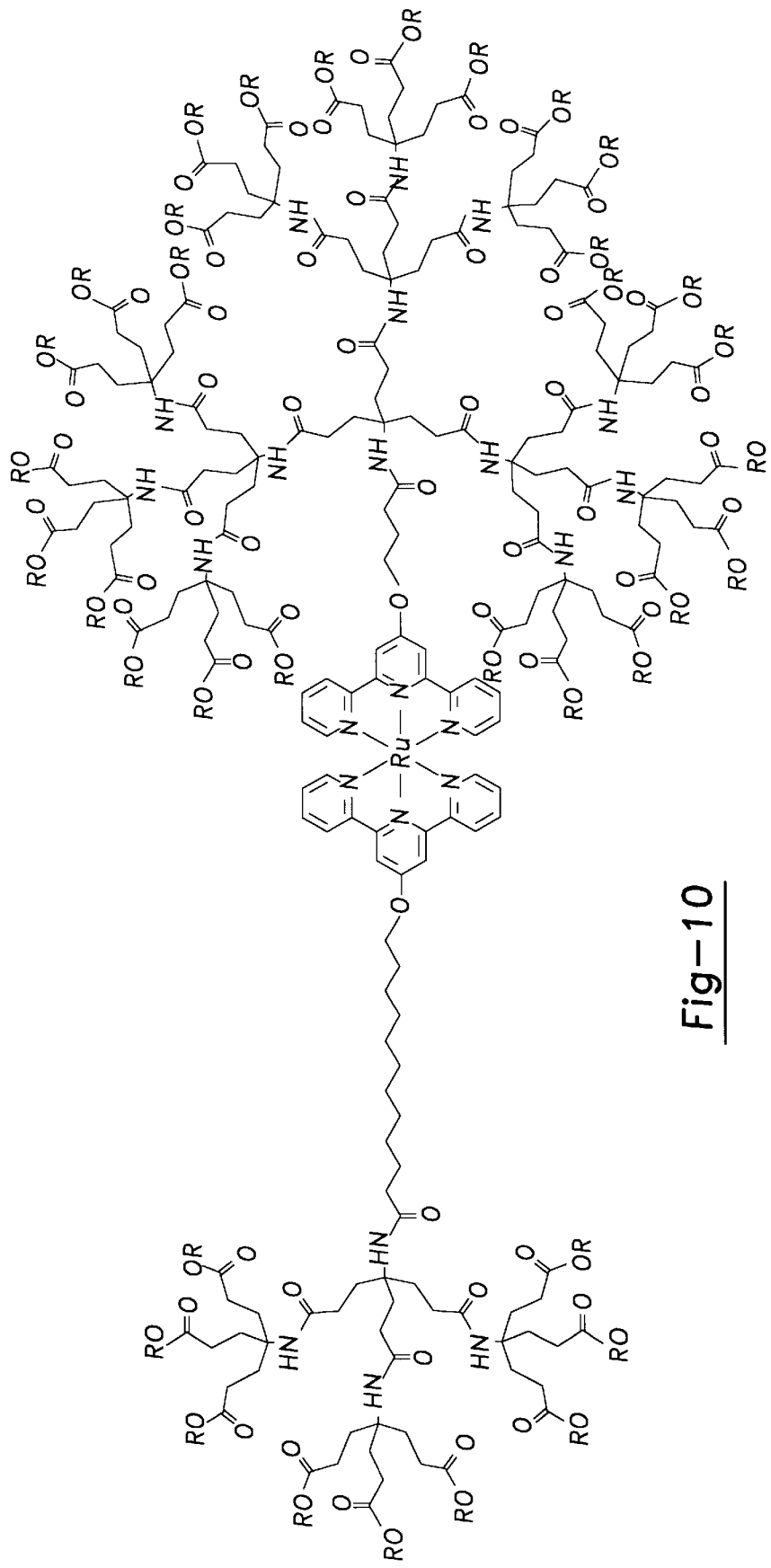
FIG. 10 shows a line drawing of the complex (VI) formed when third generation lock is treated with a second generation key.

The terpyridine ligand is non-discriminatory in complexation with metals; it does, however, form strong complexes and the metal centers can be electrochemically modified creating a potential catalytic center. The use of bipyridine and related bis-amines can generate enhanced selectivity in the recognition process. Lehn and Potts have shown the bis-, tris-, and tetrakis-bipyridines recognize only their counterpart such that the bis-bis, tris-tris, and tetrakis-tetrakis are formed selectively even though there may be a mixture of ligands. FIG. 9 depicts the key-lock combinations necessary to generate the complexed structure; the lock would be treated initially with the metal salt, followed by the introduction of the key. If the alternative formation of the metal-key it is possible to create boloamphiphile in which two keys are complexed to one (or more) metal ion(s).

It is anticipated that most organic molecules have one or more complimentary binding structures. Thus, initially the use of a locus with two or three hydrogen bonds are capable of bonding the complimentary guest with formation of the desired hydrogen bonds. Nucleic bases are used in nature to template or replicate, eg. DNA/RNA. The introduction of these same essential bases with specific locii within the void domain of these cascade macromolecules would synthetically mimic the base pairing; thus, Guanine-Cytosine (similar to the diacylaminopyridine model with the creation of three hydrogen bonds between the bases), Adenine-Thymine (2-hydrogen bonds) would act as the key/lock complimentary locus holding the complex together.

For more specific keys and locks, multiple adjacent sites enhance the specificity and/or strength of binding between the key/lock. The use of peptide chains can introduce the α-helix arrangement so that the structure(s) are flexible but capable of generating multiple hydrogen bonds between the flock and key. This α-helical structure is found in numerous proteins, e.g. the fibrous protein myosin and keratin, is easily incorporated specifically within the void domains of these macromolecules.

The following Examples demonstrate the synthesis of key and lock unimolecular micellar molecules made in accordance with the present invention.

Generally, the present invention provides a method of making physicochemically operative monomer building blocks for synthesis of cascade polymers. The method includes the steps of acylating a physicochemically operative moiety including an amino group and a multibranched core alkyne building block including an amino group with an acid chloride to form a physicochemically operative bis amide monomer including a physicochemically active portion and a branched portion. Thusly, the present invention provides a monomer or building block capable of cascade polymerization addition, whether convergent or divergent or a combination of the two, for use in the synthesis of cascade polymers.

The term "physicochemically operative moiety" is meant to mean a molecule capable of having either physiological or chemical functionality inherent unto itself. Examples of such functionalities are chelating capabilities, enzymatic capabilities, quenching capabilities, enzymatic capabilities, quenching capabilities, photosynthesizers, electron sinks, host-guest complexes as well as other chemical and physiological functions. Unexpectedly, the present invention provides a method for making a monomer to act as a synthon for the synthesis of novel cascade polymers wherein such physicochemically operative moieties are not only incorporated into the cascade polymer, but are operative moieties thereby incorporating unique utilitarian functionality into the cascade polymer.

Additionally, the resulting monomer building block includes the operative functionalities of known building blocks for making cascade polymers and, in particular, unimolecular micelles. That is, the present invention results in a cascade polymer which can function as a unimolecular micelle consisting essentially of a core atom, preferably a carbon atom, and essentially all alkyl arms extending therefrom. The result of the inventive method is a physicochemically operative monomer, including a physicochemically active portion and a branched portion and preferably, if the physicochemically operative moiety is a diamine, an amine functionality. The monomer of the present invention provides the branching and binding functionalities of a classic monomer for use in the cascade or tier elongation of a cascade polymer.

The result of the above methods produces a monomer building block of the formula

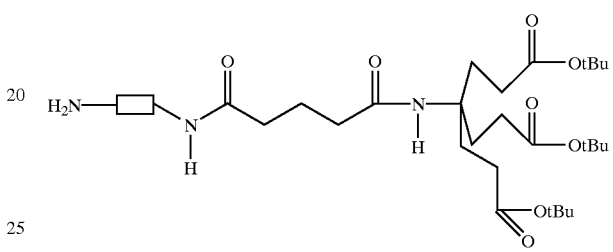

wherein

—☐— is a physicochemically operative moiety.

EXPERIMENTAL SECTION

Description of the Synthesis for the H-bonding Locks and Keys

General Procedure for the Preparation of Aminopyridine Triester Building Blocks for the Incorporation of Bis(amido) pyridine Acceptor Moieties within Cascade Superstructures. [This Procedure can be used with any bis(acid chloride).]

Aminotriester Building Block (FIG. 4)

A solution of aminotris(tert-butyl ester) (10 g, 0.024 mol) and diisopropylethylamine (3.11 g, 0.024 mol) in tetrahydrofuran (THF, 50 mL) was added to a cold (5° C.), stirred solution of glutaryl dichloride (4.07 g, 0.024 mol) in THF (900 mL) over a period of 3 h. The mixture was stirred an additional 3 h at 0–5° C.; subsequently, a mixture of THF (50 mL), 2,6-diaminopyridine (7.9 g, 0.072 mol), and diisopropylethylamine (3.11 g, 0.024 mol) was added in one portion. After stirring for another 12 h and allowing the temperature to rise to 25° C., the solvent was removed and the residue dissolved in $CH_2Cl_2$ (200 mL). Upon washing with $H_2O$ and saturated brine (2×200 mL portions of each), the organic phase was dried ($Na_2SO_4$), filtered, and the solvent was removed. Chromatography of the crude product using silica gel and $EtOAc/CH_2Cl_2$ as an eluent afforded (5.8 g, 38%) the pure aminopyridine triester. $^{13}C$ NMR ($CDCL_3$) δ 21.3 ($CH_2CH_2CH_2$), 27.9 ($CH_3$, $CH_2CO_2$), 29.7 ($CH_2CH_2CO_2$), 35.7, 36.1 ($CH_2CONH$), 57.3 [($C(CH_2)_3$], 80.5[$C(CH_3)_3$], 103.0, 104.1 [$CH(2,4)_{PYR}$], 139.7 [$CH(3)_{PYR}$], 149.7 ($CNHCO_{PYR}$), 157.2 ($CNH_{2\ PYR}$), 171.1, 171.8, 172.7 (C=O); $^1H$ NMR($ODCL_3$) δ 1.30 ($CH_2CH_2CH_2$), 1.43 ($CH_3$), 1.97 ($CH_2CO_2$), 1.30 ($CH_2CH_2CH_2$, m, 2H), 1.43 ($CH_3$, s, 27H), 1.97 ($CH_2CO_2$, m, 6H), 2.21 ($CH_2CH_2CO_2$, $CH_2CONH_{ALKYL}$, m, 8H), 2.40 ($CH_2CONH_{ARYL}$, t, 2H, 6.7 Hz), 4.56 ($NH_2$, br s, 2H), 6.09 ($NH_{ALKYL}$), 6.23 ($H_{3\ (PYR)}$, d, 1H, 7.6 Hz), 7.44 ($H_4$ & $H_{5\ (PYR)}$, m, 2H), 8.6 ($NH_{ARYL}$, br s, 1H)

General Procedure for the Preparation the First Tier Poly(pryidino) Cascades (FIG. 4; structure II).

First Tier Poly(pyridino) Dodecaester

A solution of aminopryidine triester (3.0 g, 0.0048 mol) and diisopropylethylamine (0.624 g, 0.0048 mol) in THF (10 mL) was added in one portion to a solution of tetraacid chloride (0.512 g, 0.0012 mol) in THF (5 mL) at 0° C. After stirring for 12 h, the solvent was removed and the residue was chomatographed over silica gel using combinations of EtOAc/$CH_2Cl_2$ with increasing polarities as an eluent to afford (1.6 g, 48%) the pure dodecaester (first tier lock). $^{13}$NMR($CDCL_3$) δ 21.5 ($CH_2CH_2CH_2$), 27.9 ($CH_3$, $CH_2CO_2$), 29.7 ($CH_2CH_2CO_2$), 35.8, 36.1 ($CH_2CH_2CH_2$), 37.8 ($OCH_2CH_2$), 57.3[$C(CH_2)_3$], 66.9, 69.5 ($CH_2OCH_2$), 80.5 [$C(CH_3)_3$], 109.4, 109.6 ($C_{3,5\ (ARYL)}$), 140.4 ($C_4$), 149.5, 149.7 ($C_{2,6}$), 170.5, 171.6, 172.0, 172.7 (C=O) $^1$H NMR ($CDCL_3$) δ 1.42 ($CH_3$, s, 108H), 1.98 [$C(CH_2CH_2)_3$, $CH_2CH_2CH_2$, m, 32H], 2.22 [$C(CH_2)_3$, $CH_2CH_2CH_{2EXT}$, m, 32H], 2.46, 2.59 ($CH_2CONHPYRNHCOCH_2$, 2×br t, 16H) 3.46[$C(CH_2)_4$, br s, 8H], 3.70 [($OCH_2)_4$, br t, 8H], 6.27 [$NHC(CH_2)_3$, br s, 4H], 7.62 ($PYRH_4$, t, J=8.1 Hz, 4H), 7.84 ($PYRH_3$ & $H_5$, m, 8H), 8.81, 8.89 ($NH_{PYR}$, 2 br s, 8H).

General Procedure for the Conversion of Poly(tert-butyl esters) to Poly(acids) via hydrolysis with formic acid.

First Tier Poly(pyridino) Dodecaacid

The (first tier) dodecatert-butyl ester (1.0 g, 0.36 mmol) was stirred at 40° C. for 15 h in 95% formic acid. The solvent was removed and the residue was dissolved in hot $H_2O$ (150 mL) with added charcoal and celite. The mixture was filtered through a celite pad and the clear colorless filtrate was evaporated to dryness to afford (0.70 g, 95%) the pure dodeccaacid.

$^{13}$C NMR($CD_3OD$) δ 22.7 ($CH_2CH_2CH_2$), 29.2[C ($CH_2CH_2)_3$], 30.4[$C(CH_2)_3$], 36.6, 37.1 ($CH_2CH_2CH_2$), 38.6 ($OCH_2CH_2$), 46.5 $C_{4°}$), 58.6 ($CONHC_{4°}$), 68.3 ($C_{4°}CH_2$), 70.6 ($OCH_2$), 110.6, 110.7 ($C_3$ & $C_5)_{PYR}$), 141.4 ($C_4)_{PYR}$, 151.2, 151.3 ($C_2$ & $C_6)_{PYR}$, 172.8, 174.0, 174.9, 177.2 (C=O). $^1$H NMR($CD_3OD$) δ 1.95–2.52 ($CH_2CONPYR_{INT}$, $CH_2CH_2CH_2$, $CH_2CH_2CO_2H$, m, 80H), 3.35 [$C(CH_2O)_4$, s, 8H], 3.71 [$C(CH_2OCH_2)_4$, m, 8 H], 7.70 ($H_{3,4,5(PYR)}$, m, 12H), 8.1 (NH, s).

General Procedure for the Preparation of Poly(t-butyl esters) from Poly(acids) for the formation of higher generation cascade (dendritic) locks.

Second Tier 36-tert-butyl Ester Lock

A mixture of the (first tier) dodecaacid (0.5 g, 0.24 mmol), the aminotris(tert-butyl ester) building block (1.2 g, 0.0028 mol, 12.1 eq), dicyclohexylcarbodiimide (DCC, 0.59 g, 0.0029 mol, 12.1 eq) and 1-hydroxybenzotriazol (HBT, 0.39 g, 0.0029 mol, 12.1 eq) was stirred in dry N,N-dimethylformaide (DMF, 10 mL) for 12–15 h at 25° C. After removal of the solvent, the residue was dissolved in toluene/diethyl ether (100 mL, 1:1 v/v) and washed with saturated brine (3×100 mL). The oganic phase was separated, dried ($Na_2SO_4$), filtered, and the solvent was removed. The crude material was chromatographed over silica gel eluent (EtOAc/$CH_2Cl_2$) aliquots of increasing polarity to afford (0.77 g, 48% ) the pure second tier, 36-t-butyl ester.

$^{13}$C NMR($CDCL_3$) δ 21.6 ($CH_2CH_2CH_2$), 27.9 ($CH_3$, $CH_2CO_2R$), 29.7 [($CH_2CH_2CO_2)_{G2}$, ($CH_2CON)_{G1}$], 31.5 ($CH_2CH_2CON)_{G1}$, 36.1, 37.7 ($CH_2CH_2CH_2$), 46.5 ($C_{4°}$), 57.4 ($CONHC)_{G2,G1}$, 67.0 [$C(CH_2OCH_2)_4$], 69.6 [$C(CH_2OCH_2)_4$], 80.5 [$C(CH_3)_3$], 109.8 [($C_3$ & $C_5)_{PYR}$], 140.3 [($C_4)_{PYR}$], 149.8 [($C_2$ & $C_6)_{PYR}$], 170.8, 172.7 (C=O) $^1$H NMR ($CDCL_3$) δ 1.42 ($CH_3$, s, 324H), 1.82–2.70 ($CH_2CH_2CO$, $CH_2CH_2CH_2$, $CH_2CONHPYR$, m, 224H), 3.45, 3.63 ($CH_2OCH_2$, 2 br s, 16H), 6.40, 7.30 ($NHC_4^°$), 7.68 ($C_{4(PYR)}$, m, 4H), 7.88 ($C_3$ & $C_{5(PYR)}$, m, 8H), 8.95, 9.15 ($NH_{(PYR),\ 2}$ br s, 8H).

Second Generation 36-Acid Poly(pyridino) Cascade Lock

Preparation: please see the general procedure for the conversion of tert-butyl esters to acids via formic acid.

0$^{13}$C NMR ($CD_3OD$) δ 22.6 ($CH_2CH_2CH_2$), 29.2 ($CH_2CO2$), 30.4 ($CH_2CH_2CO_2$, $CH_2CON_{G1}$), 31.7 ($CH_2CH_2CON)_{G1}$, 36.9 ($CH_2CH_2CH_2$), 38.6 ($OCH_2CH_2$), 46.4 ($C_4^°$), 58.5 ($CONHC)_{G2G1}$, 68.2 [$C(CH_2OCH_2)_4$], 70.4 [$C(CH_2OCH_2)_4$], 110.6 [($C_3$ & $C_5)_{PYR}$], 141.5 [($C_4)_{PYR}$], 151.0 [($C_2$ & $C_6)_{PYR}$], 172.9, 174.2, 175.6, 177.3 (C=O); $^1$H NMR ($CD_3OD$) δ 1.63–2.65 ($CH_2CH_2CO_{G1,G2}$, $CH_2CH_2CH_2$, m, 200H) 3.35 ($C(CH_2OCH_2)$, $CH_2CON_{core}$, $CH_2CH_2CH_2$, br s, 32H), 3.64 ($C(CH_2OCH_2$, br s, 8H), 7.73 [$H_{3,4,5\ PYR}$, br s, 12H], 7.35, 7.49, 8.15 (NH).

Synthesis and Characterization of Barbituric Acid Based Keys.

11-Bromoundecanamide-triester. A solution of 11-bromoundecanoic acid (10.00 g, 37.7 mmol) dissolved in $CH_2Cl_2$ (30 mL) was slowly added to a solution of $SOCl_2$ (7.0 mL, 94.0 mmol) in $CH_2Cl_2$ (25 mL). The mixture was refluxed for 5 h, then concentrated in vacuo to give 11-bromoundecanoyl chloride, which was used without further purification: $^1$H NMR ($CDCl_3$) δ 1.26 (bs, ($CH_2)_5$, 10H), 1.34 (m, $CH_2CH_2CH_2Br$, 2H), 1.67 (m, $CH_2CH_2COCl$, 2H), 1.81 (m, $CH_2CH_2Br$, 2H), 2.85 (t, $CH_2COCl$, J=7.2 Hz, 2H), 3.36 (t, $CH_2Br$, J=6.8 Hz, 2H); $^{13}$C NMR ($CDCl_3$) δ 24.89 ($CH_2CH_2COCl$), 27.95 ($CH_2CH_2CH_2Br$), 28.21, 28.52, 28.84, 29.02, and 29.12 (($CH_2)_5$), 32.64 ($CH_2CH_2Br$), 33.80 ($CH_2Br$), 46.92 ($CH_2COCl$), 173.47 (COCl).

A solution of 11-bromoundecanoyl chloride (10.68 g, 37.7 mmol) dissolved in $CH_2Cl_2$ (15 mL) was added to a stirred solution of di-tert-butyl 4-amino-4-[2-(tert-butoxycarboniyl)ethyl]-1,7-heptanedioate (15.7 g, 37.7 mmol), (i-Pr)$_2$EtN. (7.32 g, 56.7 mmol), and $CH_2Cl_2$ (15 mL) at 0° C. The reaction mixture was stirred for 2 h at 25° C., filtered, and the $CH_2Cl_2$ solution washed successively with brine (50 mL), cold 10% HCl (50 mL), water (50 mL), saturated $NaHCO_3$ (50 mL), then dried over anhyd $MgSO_4$, and concentrated in vacuo to give (930) 11-bromoundecanamide-triester, as a white solid: 23.24 g; mp 61.7–63.9° C.; $^1$H NMR ($CDCl_3$) δ 1.24 (bs, ($CH_2)_5$, 10H), 1.32 (m, $CH_2CH_2CH_2$3r, 2H) 1.39 (s, $OC(CH_3)_3$, 27H), 1.47 (m, $CH_2CH_2CONH$, 2H), 1.81 (m, $CH_2CH_2Br$ 2H), 1.92 (t, $CH_2CH_2CO_2$, 6H), 2.06 (m, $CH_2CONH$ 2H), 2.18 (t, $CH_2CH_2CO_{2\ 6}H$) 3.36 (t, $CH_2Br$, 2H), 5.81 (s, CONH, 1H); $^{13}$C NMR ($CDCl_3$) δ 25.67 ($CH_2CH_2CONH$), 27.98 ($OC(CH_3)_3$)) 28.05 ($CH_2CH_2CH_2Br$), 28.63, 29.17, 29.19, 29.25, and 29.28 (($CH_2)_5$), 29.75 ($CH_2CH_2CO_2$), 29.92 ($CH_2CH_2CO_2$), 32.74 ($CH_2CH_2Br$), 33.88 ($CH_2Br$), 37.48 ($CH_2CONH$), 57.18 (CONHC), 80.52 ($OC(CH_3)_3$), 172.48 (CONHC), 172.86 ($CO_2C$)

Dimethyl Malonatoamidotriester. A mixture of 11-bromoundecanamide (10.00 g, 15.1 mmol), dimethyl malonate (5.00 g, 37.8 mmol), NaI (0.565 g, 3.77 mmol), and anhyd $K_2CO_3$ (6.25 g, 45.2 mmol) in dry DMF (50 mL) was stirred at 90–100° C. for 15–24 h. Upon cooling, the mixture was filtered through celite and concentrated in vacuo to give a residue, which was dissolved in $C_6H_6$ (100 mL), washed with water (3×100 mL), dried over anhyd $MgSO_4$, and evaporated. The resulting crude material was column chromatographed on basic alumina ($C_6H_{12}$/EtAc; 85/15) to give (56%) the desired malonatotriester, as a thick oil: 6.03 g; $^1H$ NMR (CDCl$_3$) δ 1.27 (bs, (CH$_2$)$_7$, 14H), 1.44 (s, C(CH$_3$)$_3$, 27H), 1.59 (m, CH$_2$CH$_2$CONH, 2H), 1.87 (m, CH$_2$CH$_2$CHCO$_2$Me, 2H), 1.97 (t, CH$_2$CH$_2$CO$_2$, 6H), 2.11 (t, CH$_2$CONH, 2H), 2.22 (t, CH$_2$CH$_2$CO$_2$, 6H), 3.36 (t, (MeO$_2$C)$_2$CH, J=7.5 Hz 1H), 3.73 (s, CO$_2$CH$_3$, 6H); $^{13}$C NMR (CDCl$_3$) δ 25.50 (CH$_2$CH$_2$CONH), 26.61, 27.02, 27.77. (C(CH$_3$)$_3$), 28.55, 28.87, 28.96, 29.04, 29.11 (CH$_2$CH$_2$CO$_2$), 29.14, 29.51 (CH$_2$CH$_2$CO$_2$), 29.64 (CH$_2$CH), 37.17 (CH$_2$CONH), 51.39 (CH(CO$_2$Me)$_2$), 52.07 (CO$_2$CH$_3$), 56.97 (CONHC), 80.20 (C(CH$_3$)$_3$), 169.62 (CO$_2$Me), 172.36 (CONH), 172.58 (CO$_2$C(CH$_3$)$_3$).

Barbituric Acid Key—First Tier Ester

A stirred solution of the malonatotriester (1.00 g, 1.40 mmol), urea (84.1 mg, 1.40 mmol) and potassium tert-butoxide (314 mg, 2.80 mmol) in tert-butanol (5.0 mL) was refluxed for 2 h; water (10 mL) and saturated aqueous NH$_4$Cl (2 mL) was added and the mixture was concentrated in vacuo. The resulting material was extracted with CH$_2$Cl$_2$ (25 mL), dried over anhyd Na$_2$SO$_4$, and evaporated to give (90%) the barbituric acid key, as a thich oil: $^1H$ NMR (CDCl$_3$) δ 1.18 (bs, (CH$_2$)$_7$, 14H), 1.36 (s, OC(CH$_3$)$_3$, 27H), 1.47 (m, CH$_2$CH$_2$CONH, 2 H), 1.88 (m, CH$_2$CH$_2$CO$_2$ and CH$_2$CH$_2$CH, 8H), 2.14 (m, CH$_2$CH$_2$CO$_2$ and CH$_2$CONH, 8H) 3.18 (m, CH$_2$CH, 1H), 5.8–6.2 (br s, NH, 1H), 8.7 (br, NH, 2H); $^{13}$C NMR (CDCl$_3$) δ 25.75 (CH$_2$CH$_2$CONH), 27.90 (C(CH$_3$)$_3$), 29.09 (CH$_2$CH$_2$CO$_2$), 29.64 (CH$_2$CH$_2$CO$_2$), 37.29 (CH$_2$CONH), 53.10 (CH), 57.29 (CONHC), 80.60 (C(CH$_3$)$_3$), 162.38 (NHCONH), 172.91 (CO$_2$C), 173.48 (CONHC), 174.71 (CHCONH).

Barbituric Acid Key—First Tier Acid

Triester (200 mg, 0.422 mmol) was stirred with HCO$_2$H (5.0 mL) for 24 h at 25° C., concentrated in vacuo; the last traces of formic acid were removed azeotropically via addition of toluene (3×30 mL) to give the desired triacid, as a thick oil: 150 mg; $^1H$ NMR (CD$_3$OD) δ 1.35 (br s, (CH$_2$)$_{7, 14}$H), 1.63 (m, CH$_2$CH$_2$CONH, 2H), 1.89 (m, CH$_2$CH, 2H), 2.05 (t, CH$_2$CH$_2$CO$_2$H, J=6.8 Hz, 6H), 2.21 (t, CH$_2$CONH, J=7.3 Hz, 2H), 2.31 (t, CH$_2$CH$_2$CO$_2$H, J=6.8 Hz, 6H), 3.21 (t, CH, J=7.3 Hz, 1H), 5.75 (brs, NH, 1H), 7.41 (brs, NH, 2H)

Experimental Details for H-bonding Lock and Key Complexes

Preparation of the complexes: Four to one complexes were prepared for $^1H$ NMR analysis by mixing four equivalents of Key with one equivalent of Lock in the appropriate NMR solvent.

Barbituric acid key (1st tier ester)+First tier dodecaester lock: $^1H$ NMR (CDCl$_3$) δ 8.98, 9.10 [NH (pyridinocarboxamides), 2×br s, 8H (these signals were observed to be shifted downfield by at least 0.2 ppm (J. P. Mathias, E. R. Simanek, and G. M. Whitesides, J. Am. Chem. Soc. Vol. 116., pp 4326–4340, 1994)], 7.63, 7.84 (pyr-H$_{3,4,5}$, sharp multiplets, 12H, these absorptions were observed to sharpen relative to the parent Lock) All other pertinent absorptions were observed at chemical shifts listed in the experimental section.

Barbituric acid key (1st tier ester)+second tier 36-acid lock: $^1H$ NMR (DMSO-d$^6$) δ 10.05 [NH (pyridinocarboxamides), s, 8H (these signals were observed to be shifted downfield by at least 0.2 ppm ], 7.76 (pyr-H$_{3,4,5}$, br s, 12H), these absorptions were observed to sharpen and coalescese relative to the parent Lock) All other pertinent absorptions were obsevered at chemical shifts listed in the experimental section.

Synthetic Method and Experimental Details for the Preparation of Metal Coordinated Locks and Keys.

General Procedure for the Coupling of the Hydroxyalkylacids with Cltpy.

To a stirred suspension of powdered KOH (1.82 g, 32 mmol) and 4-hydroxybutyric acid, sodium salt (0.63 g, 5 mmol) dissolved in 40 ml dry DMSO, 4'-chloro-2;2':6',2"-terpyridine (1.33 g, 5 mmol) was added. The mixture was stirred for 1 h at 25° C., and then heated to 65° C. for 20 h. After cooling 40 ml of ice-water was added and the mixture was acidified to pH 6 with 10% HCl.

The precipitate that was formed was filtered, washed with water and dried in vacuo to give the pure lock-0-acid 1.1 g (66%).

General Procedure for the Amid-Coupling

A mixture of the lock-0-acid (1.34 g, 4 mmol), dicyclohexylcarbodiimide (DCC; 866 mg, 4.2 mmol), and 1-hydroxybenzotriazole (1-HBT; 567 mg, 4.2 mmol) in 20 ml DMF was stirred at 25° C. for 1 h. Di-tert-butyl-4-amino-4-[2-(tert-butoxycarbonyl)ethyl]-heptanedioate (1.66 g, 4 mmol) was added to the mixture, which was stirred at 25° C. for additional 23 h. After filtration of dicyclohexylurea, the solvent was removed in vacuo to give a residue, which was dissolved in EtOAc and filtered through a short Alumina column. The filtrate was concentrated in vacuo, and chromatographed (SiO$_2$ column) eluting with CH$_2$Cl$_2$/EtOAc to give the pure lock-3-ester as a colorless solid 1.26 g (43%).

General Procedure for the Ester-Hydrolysis

A solution of the the lock-3-ester (915 mg, 1.25 mmol) in 95% formic acid (10 ml) was stirred at 25° C. for 20 h. After concentration, toluene was added and the solution was again evaporated to remove azeotropically any residual formic acid. No further purification is necessary to give the lock-3-acid in quantitative yield.

Preparation of the Key-Ru-complex

A suspension of the key-9-ester (280 mg, 0.15 mmol), and RuCl$_3$.3H$_2$O (39 mg, 0.15 mmol) in abs. EtOH (10 ml), was refluxed for 20 h. The solvent was evaporated in vacuo and the crude product was chromatographed on an Alumina column with Methanol to give the key-3-ester RuCl$_3$ as a brown residue 177 mg (57%).

Preparation of the Key and Lock Complexes

Lock-9-ester (65.5 mg, 0.037 mmol), and 4-ethylmorpholine (4 drops) were added to a suspension of key-3-ester-RuCl$_3$ (77 mg, 0.037 mmol) in MeOH. The mixture was heated to reflux for 1.5 h and after cooling an excess of methanolic ammoniumhexafluorophosphate was added. The solvent was evaporated in vacuo and the resulting residue was chromatographed on SiO$_2$ eluting with Acetonitrile/aqu. KNO$_3$ 7:1 to give the key-9-ester-Ru-lock-9-ester-complex as a deep red solid 90 mg (65%).

Incorporation of 2,6-diamidopyridine Moieties into Dendritic Mesomolecules

This examples demonstrates the incorporation of 2,60 diamidopyridine moieties into dendritic mesomolecules and examine their ability to form H-bonded complexes with imide groups.

Preparation of early generation polypyridino dendrimers was facilitated by employing high-dilution conditions for the connection of three structural components. As shown in FIG. 11, addition of one equivalent of aminotris(tert-butyl ester) I and diisopropylethylamine to glutaryl dichloride or dodecanedioyl dichloride, followed by addition of excess 2,6-diaminopyridine yielded (35–40%) the extended dendrons 2a and 2a, respectively Evidence for the formaton of arylamine 2a includes absorptions in the $^{13}$C NMR spectrum at 47.3, 35.7, 36.1, 171.1, 171.8 and 172.7 ppm corresponding to CONHC$_4$°, 2×NHCOH$_2$, and 3×C=O, respectively. Five peaks ($^{13}$C NMR) were also recorded for the pyridine ring carbons at 103.0, 104.1 (C$_{3,5}$), 139.7 (C$_4$), 149.7 (C$_2$), and 157.2 (C$_6$) ppm. Arylamine protons (NH$_2$) were observed ($^1$H NMR) at 4.56 ppm, while the amide proton signals occurred at 6.09 [NH$_{(ALK)}$] and 8.46 ppm [NH$_{(AR)}$]. Nearly identical $^1$H and $^{13}$C NMR spectra were recorded for the related elongated amino triester 2b.

Arylamine 2a was subsequently acylated via reaction with propionoyl to give the diamidopyridine triester 3. Tetrakis-diamidopyridine 4 was then constructed by the treatment of a poly(acid chloride) (5; see FIG. 12) with 2-amino-6-N-propionoylpyridine. Support for these structures (3 and 4) included the expected NMR absorptions as well as signals corresponding to the CH$_2$CH$_3$ groups (30.6 and 9.5 ppm; $^{13}$C NMR).

Figure 12:
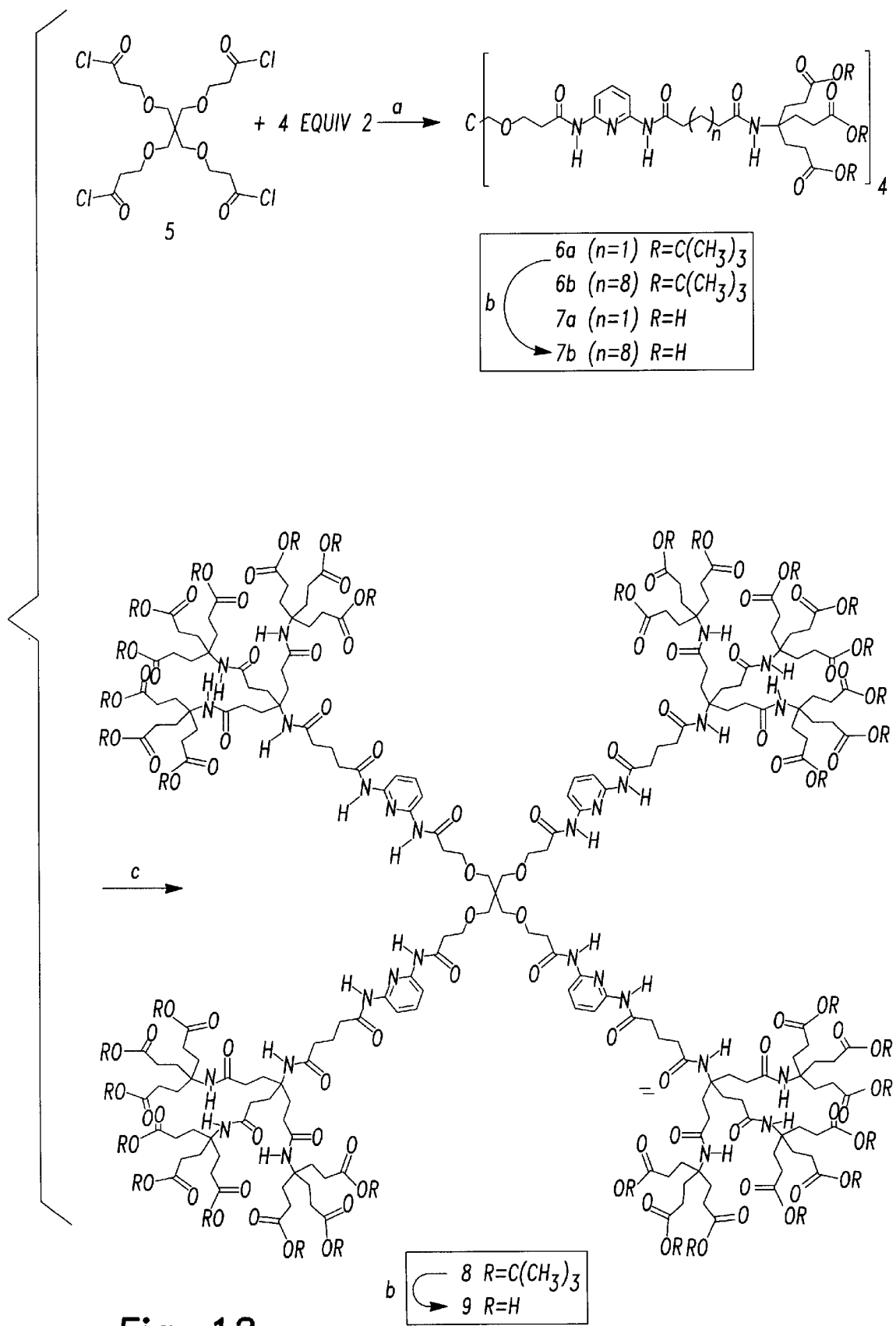
FIG. 12 shows construction of first and second tier utilitarian dendrimers possessing four 2,6-diamidopyridine unites, wherein the reagents are THF, Et(i-Pr)$_2$N, 0–25° C., 12 hours; b) HCO$_2$H, 35° C., 18 hours; c) aminotriester 1, DCC, 1-HBT, DMF, 25° C., 12 hours.

Acylation of four equivalents of the triester 2a with tetrahedral core[9] 5 provided the 1$^{st}$ tier, tetrapyridine, dodecaester 6a (FIG. 12). Formation of polyester 6a was indicated by the disappearance of $^1$H NMR peaks at 4.56 (NH$_2$) and 6.23 ppm [H$_{5(PY)}$], the appearance of absorptions at 8.89 and 8.81 ppm [2×CONH$_{(AR)}$], and the downfield shift of the signals attributed to the pyridyl protons [7.84 (H$_{3,5}$) and 7.62 ppm (H$_4$)]. Additional supporting $^{13}$C NMR resonance's included four C=O absorption's and five distinct aromatic peaks [109.4, 109.6 (C$_{3,5}$), 140.4 (C$_4$), 149.5, and 149.7 (C$_{2,6}$) ppm] suggesting a "polar gradient" proceeding from the central carbon to the periphery. Reaction of amine 2b (4 equivalent with the core 5 gave the corresponding extended dodecaester 6b as supported by similar $^1$H and $^{13}$C NMR spectra observed for 6a.

Synthesis of a second generation polypyridine dendrimer was effected by deprotection of 12-ester 6a to give dodecaacid 7a as evidenced by the disappearance of peaks attributed to the tert-butyl ester moieties followed by reaction with aimine 1 (12 equivalent) to afford 36-ester 8. Support for the conversion includes the appearance of $^{13}$C NMR signals at 27.9 (CH$_3$) and 29.2 (CH$_2$CH$_2$CO$_2$) ppm as well as at 57.4 and 80.5 ppm corresponding to the new branching C$_4$° 's and t-butyl C$_{4°,s}$ respectively. Heteroaromatic peaks appeared as broadened absorptions at 109.8 (C$_{3,5}$), 140.3 (C$_4$), and 149.8 ppm (C$_{2,6}$). The $^1$H NMR spectrum recorded the expected signasl as well as two broadened resonances at 8.95 and 9.12 ppm (pyridine carboxamide protons). Treatment of the 36-ester 6 with formic acid gave the water soluble 36-acid 7. Conversion of more lipophilic dodecaester 6b to the corresponding 12-acid 7b (HCO$_2$H)proceeded smoothly; however, repeated attempts to prepare the 2$^{nd}$ tier, 56-ester via the DCC/1-HBT acid-amine coupling were unsuccessful.

Free barbituric acid, which is only sparingly soluble in CD$_3$CN, exhibits a very broad downfield absorption for the imide moieties; whereas, it is freely soluble to the limit of complementary complexation in the presence of the bisamidopyridine dendrimers. Notably, no discernible change in the $^1$H NMR spectrum using the corresponding third tier dendrimer[9], lacking internal recognition sites, was observed in the presence of barbituric acid. Chemical shift changers for the complexed NH moieties, even in this competing solvent, corresponded to ca. 0.1 ppm for both generation dendrimers. Spectra obtained at 60° C. recorded upfield imide absorptions at 8.75 ppm suggesting internal H-bonding in the free host; thus, accounting for self association, the Δδ of the imide peak corresponds to 0.3 to 0.4 ppm.

Figure 13A:
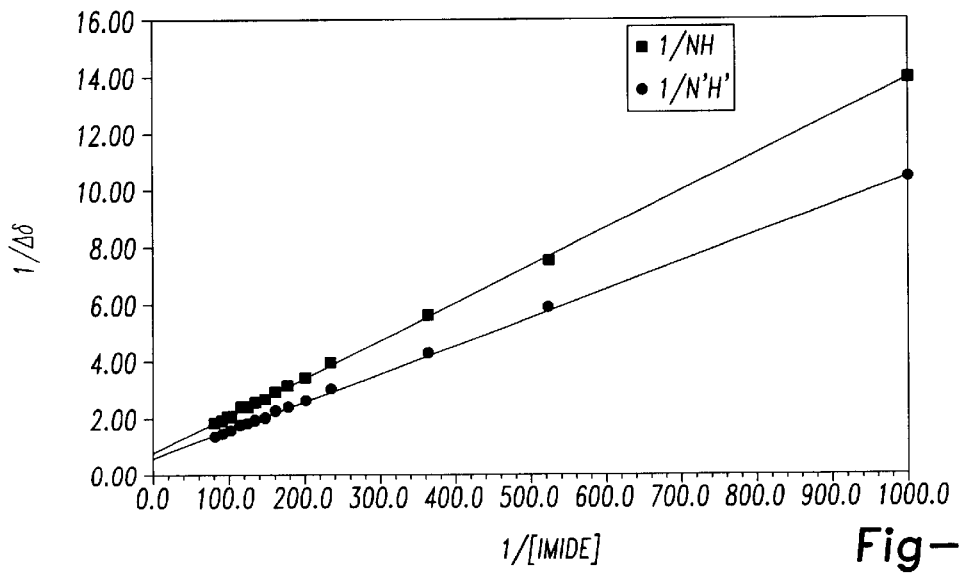
FIG. 13 shows $^1$H NMR titration data plotted for the determination of glutarimide:building block [3 (a) and 4 (b)] and dendrimer [6a (c)] H-bonding association constants.
Figure 13B:
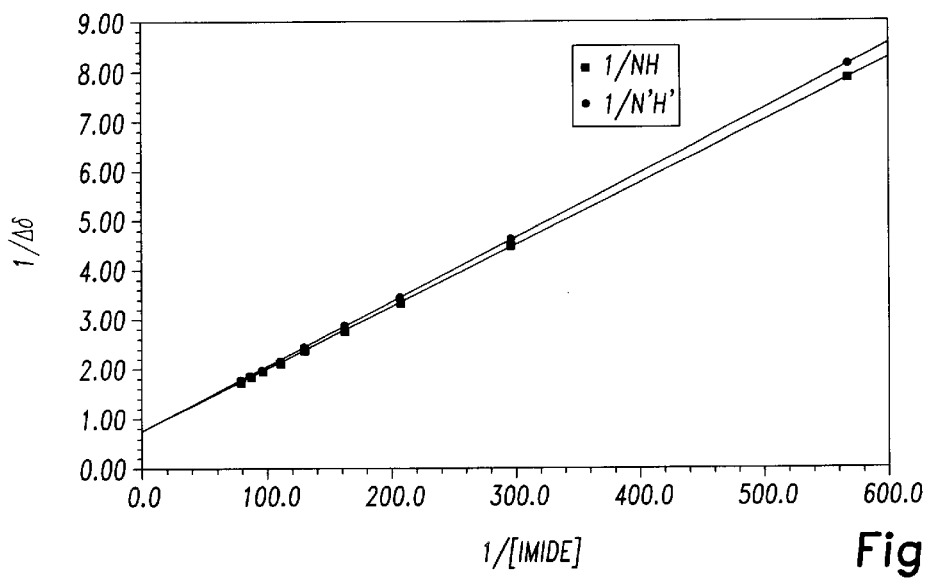
Figure 13C:
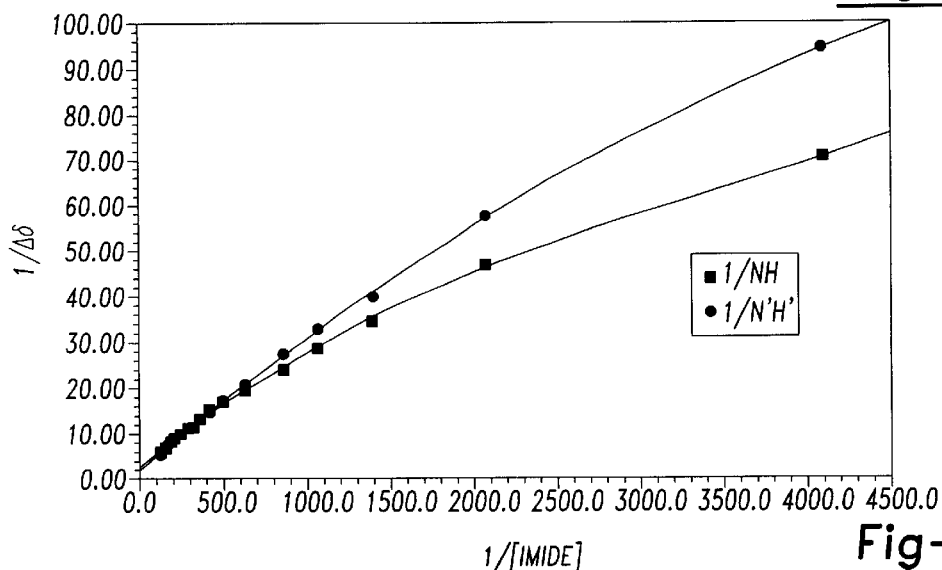

The $^1$H NMR titration experiments (in CDCl$_3$) for the determination of host (3, 4, and 6a): guest H-bonding association constants employed glutarimide primarily due to its 1:1 docking potential (unsubstituted barbituric can complicate data interpretation due to 2:1 complex formation). Glutarimide solutions were titrated with known amound of the individual hosts.[10] Chemical shift changes of the monopyridine's (3) carboxamide protons (a maximum of 0.5 and 0.7 ppm downfield for each NH) were plotted versus imide concentration (FIG. 13a). Association constants of K$_a$=62.1 and K$_a$=66.6 were determined for each NH. FIG. 13b plots the titration data using glutarimide and tetrapyridine core 4 (a maximum of 0.7 ppm for each pyridinecarboxamide NH; K$_a$=69.8 and 69.9). Constants derived from these experiments are also comparable with reported values for similar hosts:guest complexes.[3,11] FIG. 13c represents the titration of glutarimide with the first generation, tetra (bisamidopyridine) dendrimer 6a. The change in pyridinecarboxamide proton shift upon final titration with glutarimide corresponds to 0.1 and 0.2 ppm for each NH. The magnitude of these shifts corresponds well with that observed for the barbituric acid guest and further supports the postulated self association. A curved correlation suggests a more complicated guest:host relationship than in the previous examples or formulation of higher order aggregates. Other factors potentially affecting this relationship and resulting weak associations as indicated by the small NH chemical shifts [dendrimer complexation of 3'-aziod-3'-deoxythimidine (AZT) exhibited more pronounced downfield shifts of the participating protons] include inefficient donor-acceptor alignment, the potential for hos self-association, and the availability of additional complexation sites (i.e., CONH and CO$_2$R moieties; K$_a$~46 M$^{-1}$) However, these findings support specific host:guest(s) interactions; although, additional coordination sites might weakly compete for the guest(s).

Molecular modeling of the polyesters (6 and 8) reveals an ca. 20 distance (extended conformation) from the central carbon to the first tier branching point suggesting ample room for guest inclusion.

Experimental Data

The following compounds were made and analyses in accordance with the present is invention.

Lock-0-acid C$_{19}$H$_7$N$_3$O$_3$ (335)

$^1$H-NMR (CDCl$_3$/MeOD): δ=2.21 (CH$_2$, m, J=6.9 Hz, 2H), 2.59 (CH$_2$CO, t, J=7.3 Hz, 2H), 4.33 (CH$_2$Otpy, t, J=6.2 Hz, 2H), 7.46 (C$^5$H, tm, J=20 5.6 Hz, 2H), 7.93 (C$^3$H, s, 2H), 7.98 ($C^4H$, tm, J=8 Hz, 2H), 8.60 ($C^3H$, dm, J=8 Hz, 2H), 8.67 ($C_6H$, dm, J=4.9 Hz, 2H) $^{13}C$-NMR ($CDCl_3$/MeOD): δ=25.73 ($CH_2$), 31.63 ($CH_2CO$), 68.63 ($CH_2Otpy$), 108.68 ($C_3'$), 123.16 ($C^3$), 125.48 ($C^5$), 38.75 ($C^4$), 150.01 ($C^6$), 157.26 ($C^2$), 158.38 ($C^{2'}$), 168.60 ($C^{4''}$), 177.00 ($CO_2H$)

Lock-3-ester $C_{41}H_{56}N_4O_8$ (732)
$^1H$-NMR ($CDCl_3$): δ=1.40 (C($CH_3$)$_3$, s, 27H), 1.98 ($CCH_2$, t, 6H) 2.15 ($CH_2$, m, 2H), 2.21 ($CCH_2CH_2$, t, 6H), 2.35 ($CH_2CON$, t, 2H), 4.26 ($CH_2Otpy$, t, 2H), 5.99 (NH, s, 1H), 7.32 ($C^5H$, tm, 2H), 7.82 ($C^4H$, tm, 2H), 8.00 ($C^{3'}H$, s, 2H), 8.60 ($C^3H$, dm, 2H), 8.67 ($C^6H$, dm, 2H). $^{13}C$-NMR ($CDCl_3$): δ=25.06 ($CH_2$), 28.02 (C ($CH_3$)$_3$), 29.83 ($CH_2CO$), 30.05 ($CCH_2$), 33.43 ($CH_2CON$), 57.46 (C-quat), 67.22 ($CH_2Otpy$), 80.63 ($OCC(CH_3)_3$), 107.37 ($C^{3'}$) 121.28 ($C^3$), 123.74 ($C^5$), 136.70 ($C^4$), 148.99 ($C^6$), 156.10 ($C^2$), 157.12 ($C^{2'}$), 167.02 ($C^{4''}$), 171.48 (CON), 172.86 ($CO_2C(CH_3)_3$)

Lock-3-acid $C_{29}H_{32}N_4O_8$ (564)
$^1H$-NMR (MeOD)): δ=2.10 ($CH_2$; $CCH_2$, m 'br', 8H), 2.38 ($CCH_2CH_2$, t, 6H), 2.43 ($CH_2CON$, t, 2H), 4.12 ($CH_2Otpy$, t, 2H), 7.47 ($C^5H$, t, 2H), 7.70 ($C^{3'}H$, s, 2H), 7.93 ($C^4H$, t, 2H), 8.35 ($C^3H$, d, 2H), 8.60 ($C^6H$, d, 2H). $^{13}C$-NMR (MeOD): δ=26.21 ($CH_2$) 29.60 ($CH_2CO$) 30.81 ($CCH_2$), 33.75 ($CH_2CON$), 58.96 (C-quat), 69.47 ($CH_2Otpy$), 109.26 ($C^{3'}$), 123.53 ($C^3$), 126.45 ($C^5$), 139.94 ($C^4$), 149.62 ($C^6$), 154.42 ($C_2$), 155.87 ($C^{2'}$), 169.47 ($C^{4''}$), 174.87 (CON), 177.42 ($CO_2H$).

Lock-9-ester $C_{95}H_{149}N_7O_{23}$ (1755)
$^1H$-NMR ($CDCl_3$): δ=1.40 (C($CH_3$)$_3$, 81H), 1.95 ($CCH_2$, m, 24H), 2.17 ($CH_2$; $CCH_2CH_2$, m, 26H), 2.38 ($CH_2CON$, t, 2H), 4.26 ($CH_2Otpy$, t, 2H), 6.13 (NH, s 'br', 3H), 6.17 (NH, s 'br', 1H), 7.28 ($C^5H$, tm, 2H), 7.80 ($C^4H$, tm, 2H), 7.98 ($C^{3'}H$, s, 2H), 8.58 ($C^3H$, dm, 2H), 8.65 ($C^6H$, dm, 2H). $^{13}C$-NMR ($CDCl_3$): δ=25.14 ($CH_2$), 27.99 (C($CH_3$)$_3$), 29.76 ($CH_2CH_2CO$), 33.42 ($CH_2CON$), 57.41 (C-quat), 67.49 ($CH_2Otpy$), 80.46 ($OCC(CH_3)_3$), 107.44 ($C^{3'}$) 121.20 ($C^3$), 123.64 ($C^5$), 136.59 ($C^4$), 148.94 ($C^6$), 156.09 ($C^2$), 157.00 ($C^{2'}$), 167.05 ($C^{4''}$), 172.38 (CON), 172.76 ($CO_2C(CH_3)_3$), 172.99 (3CON).

Lock-9-acid $C_{59}H_{77}N_7O_{23}$ (1251) $^1H$-NMR (MeOD): δ=2.00 ($CH_2$; $CCH_2$, m, 26H), 2.30 ($CCH_2CH_2$, m, 24H), 2.48 ($CH_2CON$, t, 2H), 4.28 ($CH_2Otpy$, t, 2H), 7.50 ($C^5H$, t, 2H), 7.85 ($C^{3'}H$, s, 2H), 7.98 ($C^4H$, t, 2H), 8.52 ($C^3H$, d, 2H), 8.68 ($C^6H$, d, 2H). $^{13}C$-NMR (MeOD): δ=26.53 ($CH_2$), 29.56 ($CH_2CO$), 30.76 ($CCH_2$), 34.18 ($CH_2CON$), 58.87 (C-quat), 69.33 ($CH_2Otpy$), 109.19 ($C^{3'}$), 123.54 ($C^3$), 126.13 ($^5$), 139.55 ($C^4$), 150.02 ($C^6$), 156.07 ($C^2$), 157.07 ($C^{2'}$), 169.20 ($C^{4''}$), 175.30 (CON), 175.80 (3CON), 177.45 ($CO_2H$).

Key-0-acid $C_{27}H_{33}N_3O_3$ (447) $^1H$-NMR ($CDCl_3$): δ=1.33 ($CH_2$, s 'br', 12H), 1.50 ($CH_2$, m, 2H), 1.65 ($CH_2$, m, 2H), 1.85 ($CH_2$, m, 2H), 2.32 ($CH_2CO$, t, 2H), 4.21 ($CH_2Otpy$, t, 2H), 6.9 ($CO_2H$, 'br', 1H) 7.34 ($C^5H$, tm, J=4.9 Hz, 2H), 7.85 ($C^4H$, tm, J=7.9 Hz, 2H), 7.97 ($C^{3'}H$, s, 2H), 8.60 ($C^3H$, dm, J=7.9 Hz, 2H), 8.72 ($C^6H$, dm, J=4.9 Hz, 2H). $^{13}C$-NMR ($CDCl_3$): δ=24.79 ($CH_2$), 25.77 ($CH_2$), 28.87 (4$CH_2$), 28.97 (2$CH_2$), 29.15 ($CH_2$), 34.21 ($CH_2CO$), 68.23 ($CH_2Otpy$), 107.58 ($C^{3'}$), 121.56 ($C^3$), 123.82 ($C^5$), 136.95 ($C^4$), 148.90 ($C^6$), 156.17 ($C^2$), 156.85 ($C^{2'}$), 167.42 ($C^{4''}$), 178.06 ($CO_2H$).

Key-3-ester $C_{49}H_{72}N_4O_8$ (844) $^1H$-NMR ($CDCl_3$): δ=1.18 ($CH_2$, s 'br', 12H), 1.24 (C($CH_3$)$_3$, s, 27H), 1.30 ($CH_2$, m, 2H), 1.45 ($CH_2$, m, 2H), 1.70 ($CH_2$, m, 2H), 1.82 ($CCH_2$, t, 6H), 2.00 ($CH_2CON$, t, 2H), 2.08 ($CCH_2CH_2$, t, 6H), 4.04 ($CH_2Otpy$, t, 2H), 5.99 (NH, s, 1H), 7.15 ($C^5H$, t, 2H), 7.67 ($C^4H$, t, 2H), 7.82 ($C^3H$, s, 2H), 8.44 ($C^3H$, d, 2H), 8.50 ($C^6H$, d, 2H). $^{13}C$-NMR ($CDCl_3$): δ=25.65 ($CH_2$), 25.79 ($CH_2$), 28.87 ($CH_2$), 2913 (2$CH_2$), 29.19 ($CH_2$), 29.33 ($CH_2$), 29.37 (2$CH_2$), 29.67 ($CCH_2$), 29.85 ($CCH_2CH_2$), 37.39 ($CH_2CON$), 68.04 ($CH_2Otpy$), 80.40 ($OC(CH_3)_3$), 107.25 ($C^3$), 121.16 ($C^3$), 123.57 ($C^5$), 136.56 ($C^4$), 148.81 ($C^6$), 156.03 ($C^2$), 156.85 ($C_2'$), 166.90 ($C^4$), 172.47 (CON) 172.74 ($CO_2C(CH_3)_3$).

Key-3-acid $C_{37}H_{48}N_4O_8$ (676) $^1H$-NMR ($CDCl_3$): δ=1.28 ($CH_2$, s 'br', 12H), 1.38 ($CH_2$, m, 2H), 1.58 ($CH_2$, m, 2H), 1.72 ($CH_2$, m, 2H), 2.08 ($CCH_2$, m, 6H), 2.20 ($CH_2CO$, t, 2H) 2.34 ($CCH_2CH_2$, m, 6H), 4.00 ($CH_2Qtpy$, t, 2H), 7.41 ($C^5H$, t, 2H), 7.68 ($C^{3'}H$, S, 2H), 7.90 ($C_4H$, t, 2H), 8.40 ($C^3H$, d, 2H), 8.60 ($C^6H$, d, 2H). $^{13}C$-NMR ($CDCl_3$): δ=27.08 ($CH_2$), 27.31 ($CH_2$), 29.51(2$CH_2$), 30.10 ($CH_2$), 30.47 (2$CH_2$), 30.57 (2$CH_2$), 30.73 (6 $CCH_2CH_2$), 37.89 ($CH_2CO$), 58.68 (C-quat), 69.99 ($CH_2Otpy$), 108.90 ($C^{3'}$), 123.26 ($C^3$), 126.03 ($C^5$), 139.39 ($C^4$), 149.73 ($C^6$), 155.36 ($C^2$), 156.55 ($C^{2'}$), 169.17 ($C^{4''}$), 176.12 (CON), 177.29 ($CO_2H$).

Key-9-ester $C_{103}H_{165}N_7O_{23}$ (1867) $^1H$-NMR ($CDCl_3$): δ=1.20 ($CH_2$, s 'br', 12H), 1.30 (C($CH_3$)$_3$, s, 81H), 1.38 ($CH_2$, m, 2H), 1.50 ($CH_2$, m, 2H), 1.76 ($CH_2$, m, 2H), 1.86 ($CCH_2$, m, 24H), 2.10 ($CH_2CO$; $CCH_2CH_2$, m, 26H), 4.12 ($CH_2Otpy$, t, 2H), 5.98 (NH, s, 1H), 6.07 (NH, s, 3H), 7.21 ($C^5H$, t, 2H), 7.73 ($C^4H$, t, 2H), 7.90 ($C^{3'}H$, s, 2H), 8.50 ($C^3H$, d, 2H), 8.58 ($C^6H$, d, 2H). $^{13}C$-NMR ($CDCl_3$): δ=25.61 ($CH_2$), 25.74 ($CH_2$), 27.86 (C($CH_3$)$_3$), 28.83 ($CH_2$), 29.22 (2$CH_2$), 29.36 (3$CH_2$), 29.58 (18$CH_2$), 29.75 (6$CH_2$), 31.56 ($CH_2$), 31.89 ($CH_2CO$), 57.16 (C-quat), 67.98 ($CH_2Otpy$), 80.26 ($OC(CH_3)_3$), 107.15 ($C^{3'}$), 121.07 ($C^3$), 123.53 ($C^5$), 136.51 ($C^4$), 148.77 ($C^6$), 155.95 ($C^2$), 156.79 ($C^{2'}$), 167.11 ($C^{4''}$), 172.43 ($CO_2C(CH_3)_3$), 172.72 (3CON), 172.81 (CON).

Lock-9-ester-Ru-key-9-ester $C_{198}H_{314}N_{14}O_{46}Ru$ (3723)
$^1H$-NMR ($CDCl_3$): δ=1.30 ($CH_2$, s, 12H), 1.40 (C($CH_3$)$_3$, s, 81H), 1.43 (C($CH_3$)$_3$, s, 81H), 1.60 ($CH_2$, m 'br', 4H), 1.93 ($CH_2$, m 'br', 48H), 2.20 ($CH_2$, m, 'br', 52H), 2.55 ($CH_2$, m 'br', 4H), 4.10 ($CH_2Otpy$, t, 4H), 6.03 (NH, s 'br', 1H), 6.18 (NH, s 'br', 3H), 6.46 (NH, s 'br', 4H), 7.19 ($C^5H$, m, 4H), 7.38 ($C^4H$, m, 4H), 7.65–8.80 ($C^{3'}H$; $C^3H$; $C^6H$, m, 12H). $^{13}C$-NMR ($CDCl_3$): δ=25.89 ($CH_2$), 28.07 (C($CH_3$)$_3$), 29.79 ($CH_2$), 31.78 ($CH_2$), 32.20 ($CH_2$), 33.59 ($CH_2$), 57.21, 57.36 (C-quat), 80.36, 80.52 ($OC(CH_3)_3$), 111.13, 111.55 ($C^{3'}$), 124.52 ($C^3$), 127.72 ($C^5$), 137.82, 138.18 ($C^4$), 151.98 ($C^6$), 155.99, 156.12 ($C^2$), 158.24 ($C^{2'}$), 166.23, 168.26 ($C^{4''}$), 172.70, 172.77 ($CO_2C(CH_3)_3$), 172.95 (CON).

The above Examples demonstrate the method of making, and using the present invention. Other uses of the present invention can be achieved through the cross-linking of such molecules having multiple lock and key portions. Also, the turning on and turning off of the binding portions and specificity for binding various molecules such as drug molecules, provide for the use of the present invention as drug delivery systems where the drug is either irreversibly or reversibly bound at the acceptor site.

The invention has been described in an illustrative manner, and it is to be understood the terminology used is intended to be in the nature of description rather than of limitation.

Obviously many modifications and variations of the present invention are possible in light of the above teachings. Therefore, it is to be understood that within the scope of the appended claims, the invention may be practiced otherwise than as specifically described.

REFERENCES 1. (a) Mittal, K. et al. in *Micellization, Solubilization, and Microemulsions*, Mittal, K. L., Ed.; Plenum Press, New York, 1977; (b) Tanford, C. in *The Hydrophobic Effect: The Formation of Micelles and Biological Membranes,* 2nd Ed., Wiley-Interscience, New York, 1980; (c) Ringsdorf, H. et al., *Angew. Chem. Int. Ed. Engl.* 1988, 27, 113–158.
2. Menger, F. *Angew. Chem. Int. Ed. Engl.* 1991, 30, 1086–1099.
3. (a) Mekelburger, H., Jaworek, W., Vögtle, F. *Angew. Chem. Int. Ed. Engl.* 1992, 31, 1571–1576 (b) Buhleier, E., Wehner, W., Vögtle, F., *Synthesis,* 1978, 155.
4. Newkome, G. R., Moorefield, C. N., Baker, G. R. *Adrichimca Acta* 1992, 25, 31–38.
5. Newkome, G. R., Moorefield, C. N., Baker, G. R., Johnson, A. L., Behera, R. K. *Angew Chem. Int. Ed. Engl.* 1991, 30, 1176.
6. Newkome, G. R., Moorefield, C. N., Baker, G. R., Saunders, M. J., Grossman, S. H. *Angew Chem. Int. Ed. Engl.* 1991, 30, 1178.
7. (a) Tomalia, D. A., et al., *Macromolecules* 1987, 20, 1167–1169; (b) Tomalia, D. A., et al., *Macromolecules* 1986, 19, 2466; Tomalia, D. A., et al., *J. Am. Chem. Soc.* 1987, 109, 1601–1603.
8. Pessi, A., Bianchi, E., Bonelli, F. Chiappinelli, L. *J. Chem. Soc., Chem. Commun.* 1990, 8–9.
9. Padias, A. B., Hall, H. K. Jr., Tomalia, D. A., McConnell, J. R. *J. Org. Chem.* 1987, 52, 5305–5312.
10. Bochkov, A. F., et al., *Izv. Akad. Nauk SSSR, Ser. Khim.* 1989, 2395.
11. Rengan, K., et al. *J. Chem. Soc., Chem. Commum.* 1990, 1084–1085.
12. Uchida, H., et al., *J. Am. Chem. Soc.* 1990, 112, 7077–7079.
13. Bochkarev, M. N., et al., *J. Organomet. Chem. (USSR)* 1987, 195.
14. Wooley, K. L., et al., *J. Chem. Soc. Perkin Trans.* 1 1991, 1059–1075; Hawker, C. J., Frechet, J. M. *J. J. Am. Chem. Soc.* 1990, 112, 7638–7647; *Macromolecules* 1990, 23, 4276–4729; *J. Chem. Soc. Chem. Commum.* 1990, 1010.
15. Rajca, A. *J. Org. Chem.* 1991, 56, 2557–2563; *J. Am. Chem. Soc.* 1990, 5890, 5889–5890.
16. Kim, Y. H., Webster, O. W. *J. Am. Chem. Soc.* 1990, 112, 4592.
17. Miller, T. M., Neenan, T. X. *Chem. Mater.* 1990, 2, 346.
18. Shahlai, K., Hart, H. *J. Am. Chem. Soc.* 1990, 112, 3687–3688; *J. Org. Chem.* 1990, 55, 3412.
19. Moore, J. S., Xu, Z. *Macromolecules* 1991, 24, 5893–5894.
20. Lakowicz, J. R., Cherek, H., Maliwal, B. P. *Biochem.* 1985, 24, 376–383.
21. Shinkai, S., et al., *J. Am. Chem. Soc.* 1986, 108, 2409; Brooker, L. G. S., Sprague, R. H. *J. Am. Chem. Soc.* 1941, 63, 3214.
22. Menger, F. M. Takeshita, M., Chow, J. F. *J. Am. Chem. Soc.* 1981, 103, 5938–5939.
23. Saunders, M. J., et al., *Planta* 1981, 152, 272–281.
24. Menger, F. M., Takeshita, M., Chow, J. F. *J. Am. Chem. Soc.* 1981, 103, 5938–5939.

What is claimed is:

1. A lock unimolecular micelle including at least one void region defining a pocket and an engineered acceptor within said void region having an affinity for a complementary site of a ligand for specifically binding the ligand to the acceptor with said pocket.

2. A micelle as set forth in claim 1 wherein said acceptor is a moiety selected from a group consisting of partially charged molecules engineered to be complementary to a binding portion of a guest molecule.

3. A micelle as set forth in claim 2 wherein said acceptor is selected from the group consisting of bipyridines, tripyridines, poly Lewis base moieties comprised of oxygen, nitrogen, sulfur, phosphorous, halides, and transition metals.

4. A micelle as set forth in claim 2 wherein said acceptor includes at least one partially negative charge.

5. A micelle as set forth in claim 4 wherein said acceptor includes at least one partially positive charge.

6. A micelle as set forth in claim 1 wherein said micelle includes a plurality of branches extending therefrom, at least one of said branches including said acceptor.

7. A micelle as set forth in claim 6 wherein said branches form at least one void region therebetween, said acceptor being an integral part of at least one of said branches for binding at least a portion of the ligand within said void region.

8. A micelle as set forth in claim 7 wherein at least some of said branches extend about said acceptor defining a predetermined pocket containing said void region, said pocket being lipophilic, said pocket including an opening to an exterior of said micelle.

9. A micelle as set forth in claim 8 wherein said opening of said pocket is a predetermined distance from said acceptor for defining a specific depth that a key micelle can be inserted into said pocket to allow only binding of specific key micelles.

10. A micelle as set forth in claim 8 wherein said branches include terminal moieties, said pocket including gatekeeper molecules for allowing the entrance of only specifically structured molecules into said opening of said pocket.

11. A micelle as set forth in claim 10 wherein said gatekeeper molecules are selected from the group consisting of amino acids, carbohydrates and sugars.

12. A micelle as set forth in claim 10 wherein said gatekeeper moiety is a chiral molecule for forming a single enantiomer of a guest molecule which can enter said opening of said pocket to bind said acceptor.

13. A micelle as set forth in claim 8 wherein said branches are flexible and can extend from and retract towards said core molecule, said micelle having an outer surface including interactive moieties bound to said branches for interacting with an environment of said micelle and soluble in an environment to expand said branches and be insoluble in an altered environment to contract said micelle, said expansion of said micelle exposing said opening of said pocket and said contraction folding said branches over said opening of said pocket.

14. A micelle as set forth in claim 13 wherein said interactive moieties are soluble in response to changes in pH.

15. A micelle as set forth in claim 13 wherein said interactive moieties are soluble in response to changes in ionization.

16. A micelle as set forth in claim 14 or 15 wherein said interactive moieties are selected from the group consisting of carboxyls, amines, amides, esters, sulfonic acids, sulfates, phosphates, phosphonium, sulfonium, nitronium, onium, alcohols, sulfonamides, alkyl, aryl, and aralkyl.

* * * * *